United States Patent
Cuñé Castellana et al.

(10) Patent No.: US 10,850,135 B2
(45) Date of Patent: Dec. 1, 2020

(54) ANTISEPTIC-TOLERANT LACTIC ACID BACTERIA

(71) Applicant: AB-BIOTICS, S.A., Cerdanyola del Vallés (ES)

(72) Inventors: Jordi Cuñé Castellana, Rubi (ES); Jonathan Santas Gutiérrez, Castelldefels (ES)

(73) Assignee: AB-BIOTICS, S.A., Cerdanyola del Vallés (ES)

( * ) Notice: Subject to any disclaimer, the term of this patent is extended or adjusted under 35 U.S.C. 154(b) by 0 days.

(21) Appl. No.: 16/338,745

(22) PCT Filed: Sep. 29, 2017

(86) PCT No.: PCT/EP2017/074844
§ 371 (c)(1),
(2) Date: Apr. 2, 2019

(87) PCT Pub. No.: WO2018/065324
PCT Pub. Date: Apr. 12, 2018

(65) Prior Publication Data
US 2019/0247681 A1    Aug. 15, 2019

(30) Foreign Application Priority Data

Oct. 3, 2016 (EP) .................................. 16382453

(51) Int. Cl.
| | | |
|---|---|---|
| C12N 1/00 | (2006.01) |
| A61Q 11/00 | (2006.01) |
| A61K 35/744 | (2015.01) |
| C12N 1/20 | (2006.01) |
| C12R 1/01 | (2006.01) |
| A61K 9/00 | (2006.01) |
| A61K 9/20 | (2006.01) |
| C12Q 1/02 | (2006.01) |
| A61K 35/00 | (2006.01) |

(52) U.S. Cl.
CPC ............ *A61Q 11/00* (2013.01); *A61K 9/0056* (2013.01); *A61K 9/20* (2013.01); *A61K 35/744* (2013.01); *C12N 1/20* (2013.01); *C12Q 1/025* (2013.01); *C12R 1/01* (2013.01); *A61K 2035/115* (2013.01)

(58) Field of Classification Search
CPC ...................................................... A61Q 11/00
See application file for complete search history.

(56) References Cited

U.S. PATENT DOCUMENTS

| 2006/0153959 A1 | 7/2006 | Behan et al. |
| 2016/0030331 A1 | 2/2016 | Harvey |

FOREIGN PATENT DOCUMENTS

| KR | 20110019803 A | 3/2011 |
| WO | 2012022773 A1 | 2/2012 |
| WO | 2017012905 A1 | 1/2017 |

OTHER PUBLICATIONS

Fabricius et al (International Journal of Oncology vol. 39 pp. 1083-1097) (Year: 2011).*
International Search Report and Written Opinion in corresponding International Patent Application No. PCT/EP2-17/074844 dated Sep. 29, 2017. 12 pages.
Dunn et al. "Antimicrobial efficacy of an array of essential oils against lactic acid bacteria." Journal of food science 81.2 (2016): M438-M444. 7 pages.
Samot et al. "Antibacterial activity of probiotic candidates for oral health" Anaerobe Journal, 19.1 (2012), pp. 34-38.

* cited by examiner

*Primary Examiner* — Albert M Navarro
(74) *Attorney, Agent, or Firm* — Leason Ellis LLP

(57) ABSTRACT

The present invention relates to lactic acid bacteria strains with the ability to tolerate antiseptics. The lactic acid bacteria strains have further the capacity to antagonize the growth of oral pathogens. Particularly, the lactic acid bacteria having these features belong to *Pediococcus* genus, more particularly to *Pediococcus acidilactici* species. Thus, the strains of the present invention are useful for compositions and products in the field of personal care, and 10 particularly, for oral care, as well as, for pharmaceutical products.

13 Claims, 9 Drawing Sheets

Specification includes a Sequence Listing.

ANTISEPTIC-TOLERANT LACTIC ACID BACTERIA

CROSS-REFERENCE TO RELATED PATENT APPLICATIONS

This application is a U.S. National Stage Application under 35 U.S.C. § 371 of International Patent Application No. PCT/EP2017/074844, filed Sep. 29, 2017, which claims the benefit of priority under 35 U.S.C. Section 119(e) of European Patent Application number EP 16382453.5 filed Oct. 3, 2016, both of which are incorporated by reference in their entireties. The International Application was published on Apr. 12, 2018, as International Publication No. WO 2018/065324 A1.

FIELD OF THE INVENTION

The present invention relates to the fields of personal care, medicine and microbiology. Specifically, the present invention includes lactic acid bacteria strains particularly useful for combination with antiseptics, more particularly antiseptics for oral care.

BACKGROUND ART

A healthy mouth is a unique and invaluable asset, and yet an integrated component of general health and quality of life. However, oral health is frequently affected on a daily basis by various forms of oral diseases, mainly dental caries and periodontal disease, and occasionally by oral cancer, lesions in HIV/AIDS, mucosal and salivary gland diseases, and orofacial pain and clefts. These oral disorders are collectively the commonest chronic diseases in mankind with great impacts on vital oral functions, self-esteem, quality of life and overall health and well-being. It is currently recognized that oral diseases are worldwide epidemic and a major public health problem. An estimated 90% of the world's population suffer from some forms of oral diseases at some points in their life courses. [Jin L J et al. "Global burden of oral diseases: emerging concepts, management and interplay with systemic health" *Oral Diseases* 2016].

Periodontal disease is extremely common and encompasses a number of conditions that affect one or more of the periodontal tissues. While many different diseases affect the tooth-supporting structures, plaque-induced inflammatory lesions make up the great majority of periodontal and have traditionally been grouped into either gingivitis or periodontitis.

Gingivitis is one of the most common chronic inflammatory diseases affecting mankind with prevalence in the western population of around 75%. It is characterized by redness; swelling and frequent bleeding of the gingiva and it is caused by the accumulation of bacteria in the dento-gingival environment. This chronic inflammation may be confined to the gingiva or may develop into periodontitis when there is destruction of the tooth attachment apparatus. Thus, gingivitis always precedes periodontitis although in some individuals gingivitis may never progress to periodontitis.

Therefore, periodontal diseases begin with bacterial, biofilm-induced inflammation of the soft tissues surrounding the teeth. Bacterial biofilm, also known as dental plaque, appears in different shades of white and is combined with food debris typically found at the gingival margin bordering teeth. Biofilm is also commonly found between teeth, where its removal requires additional efforts by using dental floss and interproximal brushes. When clinically evident, bacterial biofilm is considered the primary cause and accumulation is typically proportional to the severity of inflammation. The amount of bacteria in the biofilm is correlated with the severity of periodontal disease. Certain bacteria correlated with destructive periodontal disease are considered high risk and include *Porphyromonas gingivalis, Prevotella* sp., *Treponema denticola, Fusobacterium nucleatum*, and *Tannerella forsythia*, among others [Haffajee, A D et al. "Microbial etiological agents of destructive periodontal Diseases" *Periodontology* 2000. 1994, vol. 5, pp. 78-11].

Initial periodontal treatment typically involves the physical removal of the biofilm and results in reduction of inflammation and improvement in the overall periodontal condition. Dentists and periodontists may recommend additional treatment modalities that include surgical debridement, use of localized chemotherapeutic agents, and prescription systemic antibiotic. For a physician who suspects a severe periodontal condition, recommending an antibacterial oral rinse is often a therapeutic option, especially when based on an empiric periodontal diagnosis. This strategy allows the temporary management of the periodontal condition until a dentist can evaluate the patient, establish the diagnosis, and recommend further treatment [Laudenbach et al. "Common Dental and Periodontal Diseases. Evaluation and management" *Med Clin N Am* 2014, vol. 98, pp. 1239-1260]

A common antiseptic oral rinse for bacteria-induced periodontitis is chlorhexidine gluconate 0.12%. It is common to prescribe this rinse for use twice daily for a total of 2 weeks. Although, chlorhexidine gluconate has been established as being effective against dental plaque pathogens, it is rarely recommended as a sole treatment and is typically used as an adjunct to surgical and nonsurgical treatment of bacterial plaque and calculus debridement. Moreover, patients should be informed about the potential side of effects. Chlorhexidine may irritate and damage the oral mucosa, causes discolorations and staining of the teeth and other oral surfaces, increases the formation of calculus and alters taste perception. Oral irritation and local allergy-type symptoms have been also reported. Moreover, mucosal side effects have been reported including stomatitis, gingivitis and ulcers. Consequently, use of chlorhexidine for long periods is not recommended [Flötra, L. et al. "Side effects of chlorhexidine mouth washes". Scand J Dent Res 1971, vol. 73, p. 119-125].

Other common antiseptic used in mouthwashes is triclosan ([5-chloro-2-(2,4-dichlorophenoxy)phenol). Triclosan is a non-ionic halogenated phenol, with a broad spectrum of antimicrobial activity widely used throughout North America, Europe and Asia. Triclosan is effective against many types of bacteria and certain types of fungi, preventing bacterial propagation and/or eventually resulting in cell death by mechanisms that include permeation of bacterial cell wall and targeting multiple cytoplasmic and membrane sites, including RNA synthesis and the production of macromolecules. However, triclosan is being increasingly scrutinized after concerns emerged that the compound might be harmful to human health and the environment. Potential health issues surrounding the use of triclosan include antibiotic resistance, skin irritations, endocrine disruption, increasing rates of allergies and the formation of carcinogenic by-products [Dann A B, et al. "Triclosan: environmental exposure, toxicity and mechanisms of action" Journal of Applied Toxicology 2011, vol. 31, pp. 285-311].

As an alternative to mouthwashes containing synthetic compounds, some products are formulated with 'natural' compounds, such as essential oils. For instance, Listerine® is a mixture of compounds extracted from essential oils: menthol, eucalyptol, thymol and methyl salicylate. Listerine® combats harmful bacteria such as *Streptococcus mutans, Enterococcus faecalis*, and *Eikenella corrodens* and the yeast *Candida albicans* [Vlachojannis C, et al. "A Preliminary Investigation on the Antimicrobial Activity of Listerine®, Its Components, and of Mixtures Thereof" *Phytotherapy research* 2015, vol. 29, pp. 1590-1594]. Mouthwashes with essential oils are considered safer and have less unpleasant side effect (e.g. tooth staining and calculus accumulation) than those containing chlorhexidine. However, the effectiveness at short-term treatments has been also reported to be lower. Moreover, some essential oil components can exert cytotoxic effects, thus being reasonable to suggest that products containing them should be backed up by comprehensive toxicity studies, with particular attention to the duration of exposure and the concentrations of any essential oil components involved [Vlachojannis C, et al. "Listerine® Products: An update on the efficacy and safety" *Phytotheraphy Research* 2016, vol. 30, pp. 367-373].

One of the most relevant undesirable effects of antiseptics is associated to the alterations caused in the oral microbiota as a result of their unselective antiseptic effect. Unlike antibiotics, which are selectively toxic and act at specific sites within the bacterial cell, most antiseptics do not have a distinct bacterial cell target upon which to act long-term use of antiseptic agents, especially at high concentrations, can remove biofilm and/or kill disease-associated-bacteria, but also may disrupt the natural and beneficial properties of the resident oral microflora. This can lead to a problem of dysbiosis (also called dysbacteriosis) in the oral cavity, which is a microbial imbalance that can prelude the establishment of caries or periodontal diseases. The dysbiosis hypothesis maintains that the transition from periodontal health to disease reflects changes in abundance of low abundance species in the bacterial community of the periodontal pocket. This shift in the composition of the microbial community leads to alterations in the host-microbe crosstalk sufficient to mediate destructive inflammation and bone loss. In fact, it is considered that the etiology of periodontal disease is based on three groups of factors which determine whether active periodontal disease will occur: A susceptible host, the presence of pathogenic species, and the absence of so called "beneficial bacteria." The consequent disruption of the proportional relationship between strict symbionts and pathobionts triggers the destructive cascade leading to activation of inflammation and subsequent bone destruction [Castalonga M, et al. "The oral microbiome and the immunobiology of periodontal disease and caries" *Immunology Letters* 214, vol. 12, pp. 22-38].

Therefore, it is desirable to look for alternatives or improved products that can reduce the side effects of oral mouth washes or can increase their efficacy, so lower doses are required, especially during long-term treatment.

As an alternative preventive tool, the use of probiotics has been proposed. Probiotics may be a promising area of research in periodontal therapy. Probiotics are defined as "live microorganisms that when administered in adequate amounts confer health benefits on the host". It is believed that probiotics may repopulate the beneficial bacteria, which can help kill pathogenic bacteria and fight against infection. Probiotics administered orally may benefit oral health by preventing the growth of harmful microbiota or by modulating mucosal immunity in the oral cavity. Probiotic species mostly belong to the genera *Lactobacillus* and *Bifidobacterium*.

An oral probiotic known in the market is *L. reuteri* Prodentis. A recent study indicates that oral treatment with tablets containing the probiotic strain *L. reuteri* induces a significant reduction of pro-inflammatory cytokine response and improvement of clinical parameters in most patients with chronic periodontitis [Szkaradkiewicz, A. K. et al. "Effect of Oral Administration Involving a Probiotic Strain of *Lactobacillus reuteri* on Pro-Inflammatory Cytokine Response in Patients with Chronic Periodontitis". *Arch Immunol Ther Exp* (Warsz) 2014, vol. 62, p. 495-500]. Another study had the aim of evaluating the effects of *L. reuteri*-containing probiotic lozenges as an adjunct to scaling and root planing (SRP) in chronic periodontitis patients. A reduction of *Porphyromonas gingivalis* was observed in the SRP group treated with probiotic but no changes were seen in other studied pathogenic bacteria [Teughels, W. et al. "Clinical and microbiological effects of *Lactobacillus reuteri* probiotics in the treatment of chronic periodontitis: a randomized placebo-controlled study" *Journal of clinical periodontology* 2013, vol. 40 p. 1025-35]. However, the effect of *L. reuteri* on the oral microbiota remains questionable since in a parallel study, daily intake of probiotic lozenges containing *L. reuteri* (ATCC55730 and ATCC PTA5289) did not seem to significantly affect plaque accumulation, inflammatory status or microbial composition of the biofilm during experimental gingivitis [Hallstroem, H. et al. "Effect of probiotic lozenges on inflammatory reactions and oral biofilm during experimental gingivitis". *Acta Odontologica Scandinavica* 2013, vol. 71, p. 828-833].

Another example is a recent study describing the effects of orally administered lozenges with *L. rhamnosus* GG and *B. animalis* subsp. *lactis* BB-12 on the amount of plaque, gingival inflammation and the oral microbiota in healthy young adults. The probiotic lozenge decreased both plaque and gingival index, but no probiotic-induced changes were found in the microbial compositions of saliva in either group. The conclusion is that the probiotic lozenge improved the periodontal status in terms of gingival inflammation without affecting the oral microbiota [Toiviainen, A. et al., "Impact of orally administered lozenges with *Lactobacillus rhamnosus* GG and *Bifidobacterium animalis* subsp. *lactis* BB-12 on the number of salivary *mutans* streptococci, amount of plaque, gingival inflammation and the oral microbiome in healthy adults". *Clin Oral Investig* 2015, vol. 19, p. 77-83].

Other probiotics, such as *Lactobacillus brevis* CD2, may be useful for promoting oral health and inhibiting inflammatory bone loss. However, clinical efficacy is not yet clear [Maekawa, T. et al. "Topical treatment with probiotic *Lactobacillus brevis* CD2" inhibits experimental periodontal inflammation and bone loss" *J Periodont Res* 214, vol. 44, p. 785-791].

Nadkerny et al. published in 2015 a clinical trial assessing and comparing the antiplaque and anti-inflammatory potential of a probiotic mouthwash with 0.2% chlorhexidine and saline. The probiotic mouthwash (Sporlac Plus®) is prepared by mixing a probiotic formulation containing *Lactobacillus acidophilus, Lactobacillus rhamnosus, Lactobacillus sporogenes, Bifidobacterium longum*, and *Saccharomyces boulardii* with 10 ml of distilled water commercially available at the chemist. The effect of probibtic and chlorexidine on gingival index and oral hygiene index was similar [Nadkerny P V, et al. "A comparative evaluation of the efficacy of probiotic and chlorhexidine mouthrinses on clinical inflammatory parameters of gingivitis: A randomized controlled clinical study" *J Indian Soc Periodontol* 2015 vol 16, pp. 633-639].

A recent clinical trial studied the local use of probiotics as an adjunct to scaling and root planning (SRP) in the treatment of patients with chronic periodontitis and halitosis [Penala, S. et al. "Efficacy of local use of probiotics as an adjunct to scaling and root planing in chronic periodontitis and halitosis: A randomized controlled trial" *J Res Pharm Pract.* 2016 Vol. 5(2), pp. 86-93]. Subjects were randomly assigned into the test and control groups. Test group (SRP+ probiotics) received subgingival delivery of probiotics and probiotic mouthwash, and control group (SRP+placebo) received subgingival delivery of placebo and placebo mouthwash for 15 days. Probiotic consisted in a combination of two probiotic organisms: *Lactobacillus salivarius* (2E+09 CFU) and *Lactobacillus reuteri* (2E+09 CFU) per capsule. The patients were given 28 capsules each and asked to empty the capsule into the 10 ml distilled water and asked to rinse for 1 min, daily twice for 14 days. All the clinical and microbiological parameters were reduced in both groups at the end of the study, however intergroup comparison of PD reduction (PDR) and clinical attachment gain (CAG) revealed no statistical significance except for PDR in moderate pockets for the test group. Therefore, the clinical efficacy of probiotic consumption remains questionable.

In contrast, a review in the field [Yanine, N. et al. "Effects of probiotics in periodontal diseases: a systematic review". *Clinical oral investigations* 2013, vol. 17, p. 1627-34] concludes that the effectiveness of probiotics on the prevention and treatment of periodontal diseases is questionable. For the primary outcome, probing pocket depth, there would be no clinical beneficial effect of probiotics. For secondary outcomes, probiotics have shown small benefits on plaque index and gingival inflammation. Similarly, a more recent meta-analysis concludes that, although, indicators of gingival inflammation can be positively affected by probiotic therapy, there is currently insufficient evidence supporting the use of probiotics to manage (i.e. prevent or treat) periodontal disease. More studies in this direction might thus be desirable, especially taking into consideration the effect of vehicle or dose of probiotic treatment. [Gruner, D. et al. "Probiotics for managing caries and periodontitis: Systematic Review and Meta-Analysis". *J Dent* 2016, vol. 48, pp. 16-15]. In summary, it has been seen in the prior art that probiotics may contribute in the improvement of inflammation in periodontal and gingival processes, but it remains questionable whether probiotics can have a clear clinical effect.

The article of L. Dunn et al (Journal of Food Science • Vol. 81, Nr. 2, 2016, pages M438-M444) describes test of antimicrobial efficacy of an array of essential oils (and individual oil components such as e.g. thymol) against different lactic acid bacteria (e.g. *Pediococcus acidilactici, Lactobacillus buchneri* and *Leuconostoc* citrovorum). The purpose of the article was to test if the essential oil components (e.g. thymol) can be used for properly inhibiting relevant lactic acid bacteria growth and thereby be used as preserving additives to food products. Accordingly, in the article may the presence of the lactic acid bacteria (e.g. *Pediococcus acidilactici*) in the food products be seen as unwanted. Said in other words, the article does not describe a use of a *Pediococcus* strain in combination with an antiseptic (e.g. thymol) for any practical purpose, such as e.g. prevention and/or treatment of a disorder in the oral cavity.

WO2017012905A1 (AB-BIOTICS) discloses a self-film-forming composition in powder form, which allow an adequate colonization of the probiotic in oral cavities. It does not describe a use of a *Pediococcus* strain in combination with an antiseptic (e.g. thymol) for any practical purpose, such as e.g. prevention and/or treatment of a disorder in the oral cavity.

SUMMARY OF THE INVENTION

One problem to be solved by the present invention may be seen as related to provide lactic acid bacteria (LAB), that can be administrated in treatment regimens including antiseptics. The inventors have found that *Pediococcus* strains are particularly tolerant to antiseptics.

Accordingly, a first aspect of the invention relates to a *Pediococcus* strain for use in combination with at least one antiseptic, wherein the *Pediococcus* strain has the ability to tolerate at least one antiseptic selected from the group consisting of:
  a) triclosan;
  b) an essential oil comprising at least an individual constituent selected from the group consisting of menthol, eucalyptol, thymol and methyl salicylate; and
  c) an individual constituent selected from the group consisting of menthol, eucalyptol, thymol and methyl salicylate;

wherein the *Pediococcus* strain is considered to have the ability to tolerate the antiseptic when the inhibition halo determined by disc diffusion assay observed for the *Pediococcus* strain is smaller than the inhibition halo of *Porphyromonas gingivalis*, wherein the antiseptic is in a concentration to observe an inhibition of *Porphyromonas gingivalis*; and wherein the *Pediococcus* strain and the antiseptic are formulated for a separate, sequential, concomitant administration or in admixture.

This first aspect can alternatively be formulated as use of a *Pediococcus* strain in combination with an antiseptic, wherein the *Pediococcus* strain has the ability to tolerate at least one antiseptic, as described above.

A second aspect relates to a bacterial composition which comprises from $10^4$ to $10^{12}$ cfu/g of viable cells of at least one *Pediococcus* strain, wherein the *Pediococcus* strain has at least the characteristics as defined in first aspect.

A third aspect relates to a composition according to the second aspect for use in the prevention and/or treatment of a disorder in the oral cavity.

A fourth aspect relates to a personal care product or a pharmaceutical product comprising the composition as defined in the second aspect, together with acceptable excipients and/or carriers.

A fifth aspect relates to a method for screening and isolating a lactic acid bacteria strain, comprising the following steps:
  i) assaying the ability to tolerate antiseptics of individuals of lactic acid bacteria from a pool of lactic acid bacteria strain candidates; and
  ii) selecting and isolating the lactic acid bacteria strains with an ability to tolerate antiseptics higher than that of *Porphyromonas gingivalis*.

Terms used in the claims and aspects of the invention are understood in its widely and common meaning in this description. Nevertheless, they are defined hereinafter in the detailed description of the invention.

Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. Furthermore, the present invention covers all possible combinations of particular and preferred embodiments described herein. The following examples and drawings are provided herein for illustrative purposes, and without intending to be limiting to the present invention.

DETAILED DESCRIPTION OF THE INVENTION

As explained above, it is generally recognized that antiseptics have a broad spectrum of antimicrobial activity. This allows to kill a great number of bacterial and fungal species, but they also have a negative effect on commensal or probiotic bacteria. In fact, it is known that traces of antiseptics can be found after their administration, thus also compromising the use of probiotics even after the administration of an antiseptic. Therefore, the use of lactic acid bacteria, particularly as probiotic treatment, has never been suggested to be possible in combination with antiseptics.

The present inventors have surprisingly found that *Pediococcus* strains have a higher ability to tolerate antiseptics, thus being possible to administrate the strains when antiseptics are used for therapeutic or cosmetic purposes. Without being bound to the theory, it is believed that by principle of competitive exclusion which favors the friendly bacteria, if they adhere prior to pathogenic strains, *Pediococcus* administration in combination with antiseptics can be especially effective protecting against the colonization of opportunistic pathogens.

Therefore, one aspect of the present invention provides a *Pediococcus* strain for use in combination with an antiseptic, wherein the *Pediococcus* strain has the ability to tolerate at least one antiseptic selected from the group consisting of:
  a) triclosan;
  b) an essential oil comprising at least an individual constituent selected from the group consisting of menthol, eucalyptol, thymol and methyl salicylate; and
  c) an individual constituent selected from the group consisting of menthol, eucalyptol, thymol and methyl salicylate;
wherein the *Pediococcus* strain is considered to have the ability to tolerate the antiseptic when the inhibition halo determined by disc diffusion assay observed for the *Pediococcus* strain is smaller than the inhibition halo of *Porphyromonas gingivalis*, wherein the antiseptic is in a concentration to observe an inhibition of *Porphyromonas gingivalis*; and
wherein the *Pediococcus* strain and the antiseptic are formulated for a separate, sequential, concomitant administration or in admixture.

This aspect can alternatively be formulated as use of a *Pediococcus* strain in combination with an antiseptic, wherein the *Pediococcus* strain has the ability to tolerate at least one antiseptic, as described above.

Antiseptic-Tolerant Lactic Acid Bacteria Strains

It is preferred that the *Pediococcus* strain as discussed herein is an isolated lactic acid bacteria strain. As understood by the skilled person in the present context the term "isolated" relates to that the lactic acid bacteria strain has been isolated from its natural environment—i.e. it is not present in its natural environment, so it is free from other organisms and substances present in the natural environment.

The term "tolerance" as used herein refers to the ability, whether inherited or not, of microorganisms to survive transient exposure to an antiseptic, which is often achieved by slowing down an essential bacterial process. "Tolerance" is commonly understood in the literature to the capacity of microorganisms to survive without a change in the minimal inhibitory concentration (MIC). However, it can be also understood as the reduced susceptibility of a microorganism to an antimicrobial characterized by a raised minimum inhibitory concentration (MIC), or a situation in which the antimicrobial no longer prevents microbial growth.

The term "antiseptic" as used herein refers to an antimicrobial that destroys or inhibits the growth of microorganisms in or on living tissue. The term "antimicrobial" has in the present invention the normal meaning in the field, namely, an agent that kills microorganisms or inhibits their growth. They can be further grouped according to the microorganisms they act primarily against, e.g. against bacteria (antibacterials) and against fungi (antifungals). Antiseptics are generally distinguished from antibiotics because antibiotics are generally transported through the lymphatic system to destroy bacteria within the body, and from disinfectants, which destroy microorganisms found on non-living objects.

Based on the detailed assays described in EXAMPLES 2-3, the skilled person is routinely able to repeat the assay to objectively determine whether a particular strain has the ability to tolerate antiseptics. Particularly, EXAMPLE 2 provides a method to determine whether the strain is able to tolerate the antiseptic wherein the tolerance is expressed as inhibition halo determined by disc diffusion assay. For example, the *Pediococcus* strain is considered to have the ability to tolerate the antiseptic when the inhibition halo determined by disc diffusion assay observed for the *Pediococcus* strain is smaller than the inhibition halo of *Porphyromonas gingivalis*, wherein the antiseptic is in a concentration to observe an inhibition of *P. gingivalis*.

In some embodiments, the *Pediococcus* strain will be considered to have the ability to tolerate the antiseptic when the diameter of the inhibition halo determined by disc diffusion assay for the *Pediococcus* strain is at least 1 mm, 2 mm, 3 mm or 4 mm smaller than the diameter determined for *P. gingivalis*. In a more particular embodiment, the diameter of the inhibition halo observed for the *Pediococcus* is at least 4 mm smaller than the diameter of the inhibition halo determined for *P. gingivalis*.

The *Pediococcus* strains provided by the invention are characterized for having the ability to tolerate at least one of the antiseptics described in the first aspect. However, it is important to note that besides this ability, the strains can also be tolerant for other relevant antiseptics, as it is shown in the Examples. It means that the feature described in the first aspect can be considered as the key feature or marker to define a group of *Pediococcus* strains useful for the purposes of the invention.

Through the examples, different strains are provided for complying with this ability to tolerate antiseptics in a better way than *P. gingivalis*. Further to said strains, by means of the method described in detail, it is plausible to identify and isolate other strains within a pool of LAB, with the same ability to tolerate antiseptics. It is also demonstrated by means of the Examples, that the feature of tolerance to antiseptics is beneficial for the purposes of the invention. Thus, although some specific strains have been tested and identified with this beneficial feature, there is no reason to limit the scope of the invention to such strains because all the steps of the method to get other good strains are plausibly described herein. Therefore, the invention also provides a pool of strains other than the used in the Examples that have the same feature. It is important to note that not all the LAB strains will have the ability to tolerate antiseptics; thus, the invention provides a method to recognize them.

Similarly, it is relevant to note that the use of disc diffusion assay and conditions of the assay disclosed in EXAMPLES 2 is not limiting the scope of the invention. The assay is one suitable to test the ability of strains to tolerate antiseptics. The concentrations and amounts of antiseptics will be selected by the skilled person to test the tolerance of strains depending on the antiseptic to be tested. Particularly, the concentrations and amounts of antiseptics to be used will be those necessary to observe an inhibition of *P. gingivalis*.

Triclosan (CAS registration number 3380-34-5) (TCS), is a diphenyl ether and may be referred to as 2,4,4'-Trichloro-2'-hydroxydiphenyl ether, 5-Chloro-2-(2,4-dichlorophenoxy)phenol or Triclosanum. The molecular formula for TCS is C12H7Cl3O2 and the chemical has a molecular weight of 289.55. Most commercially obtained grades of TCS are over 99% pure and are available in the solid form as a white to off-white crystalline powder with a barely detectable aromatic odor. Triclosan is effective against many types of bacteria and certain types of fungi, preventing bacterial propagation and/or eventually cell death. It permeates the bacterial cell wall and targets multiple cytoplasmic and membrane sites, including RNA synthesis and the production of different biomolecules.

Essential oils are also used as alternative antiseptics, particularly for oral care. "Essential oils" (EOs) as defined herein, are oils obtained from plant or animal sources, or their synthetic equivalents, and are composed of complex mixtures of several constituents such as monoterpene and sesquiterpene hydrocarbons, monoterpene and sesquiterpene alcohols, esters, ethers, aldehydes, ketones, oxides and the like.

"Individual constituents of essential oils" are compounds that may be isolated from the oil (natural) or may be entirely or partially chemically synthetic.

Menthol may be also referred as 2-Isopropyl-5-methylcyclohexanol or 5-Methyl-2-(1-methylethyl)cyclohexanol, and is an organic compound made synthetically or obtained from corn mint, peppermint, or other mint oil.

Eucalyptol is a cyclic ether and a monoterpenoid, which is particularly abundant in essential oils of plants from genus *Eucalyptus*. Eucalyptol is also known by a variety of synonyms: 1,8-cineol, 1,8-cineole, cajeputol, 1,8-epoxy-p-menthane, 1,8-oxido-p-menthane, eucalyptol, eucalyptole, 1,3,3-trimethyl-2-oxabicyclo[2,2,2]octane, cineol, cineole.

Thymol (also known as 2-isopropyl-5-methylphenol) is a natural monoterpene phenol derivative of cymene, isomeric with carvacrol, found in oil of thyme, and extracted from *Thymus vulgaris* (common thyme) and various other kinds of plants as a white crystalline substance of a pleasant aromatic odor and strong antiseptic properties Methyl salicylate is an organic ester naturally produced by many species of plants, particularly wintergreens. Methyl salicylate is also commonly referred as methyl 2-hydroxybenzoate, *gaultheria* oil, wintergreen oil or *betula* oil.

In one embodiment, the *Pediococcus* strain further has the ability to tolerate an antiseptic from the group of bisguadines.

"Bisguanides" are a class of chemically related compounds known for their bactericidal properties. These compounds include the antiseptics alexidine and chlorhexidine. Alexidine may be also referred as 1-[N'-[6-[[amino-[[N'-(2-ethylhexyl)carbamimidoyl]amino]methylidene]amino]hexyl]carbamimidoyl]-2-(2-ethylhexyl)guanidine. Chlorhexidine is a cationic polybiguanide and may be also referred as (1E)-2-[6-[[amino-[(E)-[amino-(4-chloroanilino)methylidene]-amino]methylidene] amino] hexyl]-1-[amino-(4-chloroanilino)methylidene]guanidine.

More particularly, the *Pediococcus* strain has the ability to tolerate chlorhexidine gluconate.

The inventors have also found that *Pediococcus* strains can also have ability to inhibit the growth of bacterial pathogens (i.e. antagonize) particularly pathogens of the buccal cavity. This allows the *Pediococcus* strains to be particularly useful to avoid the colonization of pathogens and even inhibit their growth, thus improving the microbiota profile.

Thus, in one embodiment the *Pediococcus* strain further has the ability to antagonize at least one pathogen selected from the group consisting of *Fusarium nucleatum*, *Treponema denticola* and *Prevotella denticola*. Particularly, the *Pediococcus* strain has the ability to antagonize at least two of these pathogens. More particularly, the *Pediococcus* strain has the ability to antagonize *F. nucleatum*, *T. denticola* and *P. denticola*.

In one particular embodiment, the *Pediococcus* strain further has the ability to antagonize *Tannerella forsythia*.

In one particular embodiment, the *Pediococcus* strain further has the ability to antagonize *Porphyromonas gingivalis*.

Based on the detailed assay described herein (see EXAMPLE 4 for the antagonistic activity assay) the skilled person is routinely able to repeat this assay to objectively determine whether a strain of interest antagonize pathogens. Descriptions and conditions of the antagonistic activity assay are not limiting the scope of the invention. The assay is one suitable to test the ability of the strains of interest to antagonize pathogens.

"In a particular embodiment, the *Pediococcus* strain is a *Pediococcus acidilactici* strain. More particularly, the *Pediococcus* strain is a *Pediococcus acidilactici* deposited in the Spanish Type Culture Collection Colección Espanola de Cultivos TIPO (CECT), Edificio 3 CUE, Parc Cientific Universitat de Valencia, Catedratico Agustín Escardino, 9, 46980 Paterna (Valencia) ESPAÑA, on Sep. 25, 2014, under the accession number CECT 8633."

Thus, one aspect of the present invention is related to a strain belonging to *Pediococcus acidilactici* species deposited in the Spanish Type Culture Collection under accession number CECT 8633.

Another aspect of the present invention provides a composition which comprises from $10^4$ to $10^{12}$ cfu/g of viable cells of at least one *Pediococcus* strain, wherein the *Pediococcus* strain has at least the characteristics (i.e. the ability to tolerate antiseptics) as defined in the first aspect.

Compositions of the present invention may comprise a single strain or be a combination of different LAB strains belonging to the same or different species. In a particular embodiment, the *Pediococcus* strain of the present invention is found in combination with a strain of *Lactobacillus plantarum* and/or a strain of *Lactobacillus brevis*. More particularly, the composition comprising the *Pediococcus* strains of the present invention, further comprises a strain of *Lactobacillus plantarum* deposited in the Spanish Type Culture Collection under the accession number CECT 7481 and a strain of *Lactobacillus brevis* deposited in the Spanish Type Culture Collection under the accession number CECT 7480.

It is clear that by using the deposited strains as starting material, the skilled person in the art can routinely, by conventional mutagenesis or re-isolation techniques, obtain further variants or mutants thereof that retain or enhance the herein described relevant features and advantages of the strains forming the composition of the invention. Thus the invention also relates to variants of strains disclosed herein. As used herein, the term "variant" or "mutant" of a strain refers to any naturally-occurring or specifically developed strain obtained from the reference strain X, mainly by mutation, that maintains a similar ability to tolerate antiseptics than the strain.

For example, the 16S rRNA gene of a "variant" strain as contemplated herein may share about 85 percent, 86 percent, 87 percent, 88 percent, 89 percent, 90 percent, 91 percent, 92 percent, 93 percent, 94 percent, 95 percent, 96 percent, 97 percent, 98 percent or 99 percent sequence identity with the 16S rRNA sequence SEQ ID NO: 1 of a strain disclosed herein.

In another embodiment, the degree of relatedness between the variant and the parent strains is determined as the degree of similarity obtained when analysing the genomes of the parent and of the variant strain by Pulsed-field gel electrophoresis (PFGE) using one or more restriction endonucleases. The degree of similarity obtained by PFGE can be measured by the Dice similarity coefficient. In some embodiments, the Dice similarity coefficient between the variant and the parent strain is of about 95 percent, about, 96 percent, about 97 percent, of about 98 percent, of about 99 percent, of about 99, 1 percent, of about 99.5 percent, of about 99.6 percent, of about 99.7 percent, of about 99.8 percent, of about 99.9 percent, of about 99.99 percent, of about 99.999 percent, of about 99.9999 percent, of about 99.99999 percent, of about 99.999999 percent or more but less than 100 percent.

In one particular embodiment, the mutants are obtained by using recombinant DNA technology. In another embodiment, the mutants are obtained by random mutagenesis. Thus, another aspect of the invention relates to a method to obtain a mutant of a *Pediococcus acidilactici*, wherein the strain is the strain CECT 8633, wherein the method comprises using the deposited strain as starting material and applying mutagenesis, and wherein the obtained variant or mutant further retains or enhances at least the ability of the deposited strain to tolerate antiseptics.

In a particular embodiment, the strains have been fermented in an artificial medium and submitted to a post-treatment after the fermentation, to obtain bacterial cells, and the resulting bacterial cells are in a liquid medium or in a solid form. Particularly, the post-treatment is selected from the group consisting of: drying, freezing, freeze-drying, fluid bed-drying, spray-drying and refrigerating in liquid medium, and more particularly, is freeze-drying.

The strains of the invention are produced by cultivating (or fermenting) the bacteria in a suitable artificial medium and under suitable conditions. By the expression "artificial medium" for microorganisms is to be understood a medium containing natural substances, and optionally synthetic chemicals such as the polymer polyvinyl alcohol which can reproduce some of the functions of serums. Common suitable artificial media are nutrient broths that contain the elements including a carbon source (e.g. glucose), a nitrogen source (e.g. amino acids and proteins), water and salts needed for bacterial growth. Growth media can be liquid form or often mixed with agar or other gelling agent to obtain a solid medium. The strains can be cultivated alone to form a pure culture, or as a mixed culture together with other microorganisms, or by cultivating bacteria of different types separately and then combining them in the desired proportions. After cultivation, and depending on the final formulation, the strains may be used as purified bacteria, or alternatively, the bacterial culture or the cell suspension may be used, either as such or after an appropriate post-treatment. In this description, the term "biomass" is understood the bacterial strains culture obtained after cultivation (or fermentation as a term synonymous to cultivation).

By the term "post-treatment" is to be understood in the context of the present invention, any processing carried out on the biomass with the aim of obtaining storable bacterial cells. The objective of the post-treatment is decreasing the metabolic activity of the cells in the biomass, and thus, slowing the rate of cellular deleterious reactions. As a result of the post-treatment, the bacterial cells can be in solid or liquid form. In solid form, the stored bacterial cells can be a powder or granules. In any case, both the solid and liquid forms containing the bacterial cells are not present in the nature, hence, are not naturally-occurring, since they are the result of artificial post-treatment process(es). The post-treatment processes may in particular embodiments require the use of one or more of so-called post-treatment agent. In the context of the present invention, the expression "post-treatment agent" refers to a compound used to perform the herein described post-treatment processes. Among the post-treatment agents are to be included, without limitation, dehydrating agents, bacteriostatic agents, cryoprotective agents (cryoprotectants), inert fillers (also known as lyoprotectants), carrier material (also known as core material), etc., either used alone or in combination.

There are two basic approaches to decrease the metabolic activity of the bacterial cells, and thus, two approaches to carry out the post-treatment. The first one is decreasing the rate of all chemical reactions, which can be done lowering the temperature by refrigerating or freezing using refrigerators, mechanical freezers, and liquid nitrogen freezers. Alternatively, decreasing the rate of all chemical reactions can be achieved by adding substances that inhibit the growth of the bacterial cells, namely a bacteriostatic agent, abbreviated Bstatic.

The second approach to carry out the post-treatment is to remove water from the biomass, a process which can involve sublimation of water using a lyophilizer. Suitable techniques to remove water from the biomass are drying, freeze-drying, spray-drying or fluid bed-drying. Post-treatments that result in solid form may be drying, freezing, freeze-drying, fluid bed-drying, or spray-drying.

The post-treatment is preferably freeze-drying, which involves the removal of water from frozen bacterial suspensions by sublimation under reduced pressure. This process consists of three steps: pre-freezing the product to form a frozen structure, primary drying to remove most water, and secondary drying to remove bound water. Due to objective and expected variability of industrial processes for manufacturing and isolation of lyophilized bacterial cultures, the latter commonly contain certain amount of inert filler also known as lyoprotectant. Its role is to standardize the content of live probiotic bacteria in the product. The following inert fillers in commercially available lyophilized cultures are used: sucrose, saccharose, lactose, trehalose, glucose, maltose, maltodextrin, corn starch, inulin, and other pharmaceutically acceptable non-hygroscopic fillers. Optionally, other stabilizing or freeze-protecting agents like ascorbic acid, are also used to form a viscous paste, which is submitted to freeze-drying. In any case, the so-obtained material can be grinded to appropriate size, including to a powder.

Use of Lactic Acid Bacteria in Combination with an Antiseptic

As described above, the *Pediococcus* strains of the present invention are able to tolerate antiseptics, thus being suitable for use in combination with antiseptics. Examples of antisepticals include, without limitation, triclosan, botanical extracts and essential oils, bisguanides and cetylpyridinium.

In one particular embodiment, the *Pediococcus* strain is used in combination with triclosan.

In another particular embodiment, the *Pediococcus* strain is used in combination with essential oils. Examples of them include, but are not limited to, cinnamon oil, basil oil, bergamot oil, clary sage oil, ylang-ylang oil, neroli oil, sandalwood oil, frankincense oil, ginger oil, peppermint oil, lavender oil, jasmine absolute, geranium oil bourbon, spearmint oil, clove oil, patchouli oil, rosemary oil, rosewood oil, sandalwood oil, tea tree oil, vanilla oil, lemongrass oil, cedarwood oil, balsam oils, tangerine oil, Hinoki oil, Hiba oil, ginko oil, *eucalyptus* oil, lemon oil, orange oil, sweet orange oil, pomegranate seed oil, manuka oil, citronella oil, wintergreen oil and calendula oil. In a more particular embodiment, the *Pediococcus* strain is used in combination with an essential oil selected from the group consisting of peppermint oil, *Eucalyptus* oil, thyme oil, and wintergreen oil.

In one particular embodiment, the *Pediococcus* strain is used in combination with "individual constituents of essential oils". Examples of "individual constituents of essential oils" include, but are not limited to, thyme, oregano, curcumin, 1-citronellol, a-amylcinnamaldehyde, lyral, geraniol, farnesol, hydroxycitronellal, isoeugenol, eugenol, camphor, eucalyptol, linalool, citral, thymol, limonene and menthol. Further examples of individual constituents include sesquiterpenoid compounds, which may be the active compounds in the essential oils. Sesquiterpenoid compounds, containing 15 carbons, are formed biosynthetically from three 5-carbon isoprene units. Sesquiterpenoid compounds include, but are not limited to, farnesol, nerolidol, bisabolol, apritone, chamazulene, santalol, zingiberol, carotol, and caryophyllen. In a more particular embodiment, the *Pediococcus* strain is used in combination with an individual constituent of essential oil selected from the group consisting of menthol, eucalyptol, thymol and methyl salicylate.

In one particular embodiment, the *Pediococcus* strain is used in combination with bisguadines, more particularly alexidine or chlorhexidine. Alexidine and chlorhexidine are used primarily as its salts. Chlorhexidine salts according to the invention include, but are not limited to, chlorhexidine palmitate, chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-alpha-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, and chlorhexidine embonate. In a more particular embodiment, the *Pediococcus* strain is used in combination with chlorhexidine, more particularly chlorhexidine gluconate.

The strains and antiseptics of the present invention can be formulated for a separate, sequential, concomitant administration or in admixture.

The administration regimens and forms will be determined by the skilled in the art according to the disorder to be treated. Administration of antiseptics and lactic acid bacteria can be administered separately (waiting a time interval between the administration of the *Pediococcus* strain and the antiseptic), sequentially (one after the other), concomitantly (simultaneously) or in admixture (together).

In one embodiment, the antiseptic and the strains of the invention are administered within a time interval no longer than 12 hours. Particularly, the time interval is no longer than 6 hours. More particularly, the time interval is no longer than 1 hours. More particularly, the time interval is no longer than 10 minutes. In a more particular, embodiment the therapeutic regimen is based on the simultaneous administration of the antiseptic and the strains. One typical administration regimen consists in administering the antiseptic and subsequently administering the *Pediococcus* strain of the present invention. In some embodiments, the antiseptic and the *Pediococcus* strain are administered at the same time. When the antiseptic and the lactic acid bacteria are administered to the patient at the same time, they can be administered as separate forms or as a part of a single composition. When the products are administered in separate dosage forms, the dosage forms can be in the same or different containers.

In a particular administration treatment, the subject to be treated is instructed to gargle their mouth with a mouthwash containing an antiseptic (e.g. chlorhexidine at a concentration of 0.12% (w/v)) for 30-60 seconds. Then, the mouthwash is split out and oral tablet containing the lactic acid bacteria introduced in the mouth and allowed to melt slowly.

The administration can be chronic or intermittent, as deemed appropriate by the supervising practitioner, particularly in view of any change in the disease state or any undesirable side effects. "Chronic" administration refers to administration of the composition in a continuous manner while "intermittent" administration refers to treatment that is done with interruption.

In non-limiting embodiments, the *Pediococcus* strains and compositions of the present invention are used by the dental professional in an acute treatment and the patient can follow a maintenance treatment with oral care products such as chewing gums, a tooth-paste, a mouth wash, mouth spray, lozenges or oral dispersible tablets comprising the self-film-forming composition in powder form of the invention or the lactic acid bacteria with common excipients. The administration by the dental professional can be performed, for example, applying the compositions of the present invention by means of a syringe, particularly with a blunt tip needle. Other non-limiting examples of professional administrations are the application of a mouth splint containing a gel comprising the compositions of the present invention, or applying the composition formulated as a varnish on teeth surfaces by using a brush. In applications such as halitosis, periodontitis, gingivitis, or caries, the compositions of the invention can also be applied by the patient itself.

In one particular embodiment the antiseptic is in a concentration ranging from 0.05 to 0.5% (w/w). More particularly, the concentration of the antiseptic is in the range from 0.05 to 0.2% (w/w). More particularly, the concentration is 0.05, 0.1, 0.12 or 0.2% (w/w).

One aspect of the present invention provides a kit of parts comprising: a) a first vial comprising an antiseptic; and b) a second vial comprising at least a *Pediococcus* strain. In a particular embodiment, the kit further comprises instructions for use, more particularly comprising information related to dosage and/or administration regimens.

Personal Care Products

In one aspect the present invention provides personal care products that comprise the strains and compositions of the present invention together with acceptable excipients and/or carriers. The term "personal care products" refers to products used in personal hygiene and/or for beautification (cosmetics).

As understood by the skilled person in the present context the personal care products comprise an affective amount of the strains of the present invention. An effective amount of *Pediococcus* strains will be determined by the skilled in the art and will vary with the particular goal to be achieved, the age and physical condition of the patient being treated, the severity of the underlying disorder, and the final formulation. For instance, in oral health products, the strain or strains are present in an amount from about $10^5$ cfu/g to about $10^{12}$ cfu/g, particularly in an amount from about $10^7$ cfu/g to about $10^{11}$ cfu/g. The term "colony forming unit" ("cfu") is defined as number of bacterial cells as revealed by microbiological counts on agar plates. In a particular embodiment, the composition comprises between $10^7$-1010 cfu/g.

The term "excipient" is understood in its widely meaning in this description, including any natural or synthetic substance formulated alongside the active ingredient of a pharmaceutical product, veterinary product, a medicament, food supplement, medical food and personal hygiene product. The most appropriate excipient(s) to be used depend(s) of the final formulation.

Non-limiting examples of personal care products which may utilize the invention include bar soap, liquid soap (e.g., hand soap), hand sanitizer (including rinse off and leave-on alcohol based and aqueous-based hand disinfectants), cotton swabs and pads, shaving cream, talcum powder, toiled paper, preoperative skin disinfectant, wet paper, cleansing wipes, disinfecting wipes, body wash, acne treatment products, antifungal diaper rash cream, antifungal skin cream, shampoo, conditioner, cosmetics deodorant, antimicrobial creams, body lotion, hand cream, topical cream, aftershave lotion, skin toner, oral hygiene products, sunscreen lotion, and baby products such as, but not limited to, cleansing wipes, baby shampoo, baby soap, and diaper cream.

The present invention may also be applied to wound care items, such as, but not limited to, wound healing ointments, creams, and lotions, wound coverings, burn wound cream, bandages, tape, and steri-strips, and medical articles such as medical gowns, caps, face masks, and shoe-covers, surgical drops, etc.

In one particular embodiment, the personal care product is a topical cream or gel.

In various non-limiting embodiments of the invention, a personal care product comprising the compositions of the present invention may further comprise a thickening and/or gelling agent such as stearyl alcohol, cationic hydroxy ethyl cellulose (Ucare; JR30), hydroxy propyl methyl cellulose, hydroxy propyl cellulose (Klucel), chitosan pyrrolidone carboxylate (Kytamer), behenyl alcohol, zinc stearate, emulsifying waxes, including but not limited to Incroquat and Polawax, an addition polymer of acrylic acid, a resin such as Carbopol® ETD™ 2020, guar gum, acacia, acrylates/steareth-20 methacrylate copolymer, agar, algin, alginic acid, ammonium acrylate co-polymers, ammonium alginate, ammonium chloride, ammonium sulfate, amylopectin, attapulgite, bentonite, C9-15 alcohols, calcium acetate, calcium alginate, calcium carrageenan, calcium chloride, caprylic alcohol, carbomer 910, carbomer 934, carbomer 934P, carbomer 940, carbomer 941, carboxymethyl hydroxyethyl cellulose, carboxymethyl hydroxypropyl guar, carrageenan, cellulose, cellulose gum, cetearyl alcohol, cetyl alcohol, corn starch, damar, dextrin, dibenzlidine sorbitol, ethylene dihydrogenated tallowamide, ethylene diolamide, ethylene distearamide, gelatin, guar gum, guar hydroxypropyltrimonium chloride, hectorite, hyaluronic acid, hydrated silica, hydroxybutyl methylcellulose, hydroxyethylcellulose, hydroxyethyl ethylcellulose, hydroxyethyl stearamide-MIPA, isocetyl alcohol, isostearyl alcohol, karaya gum, kelp, lauryl alcohol, locust bean gum, magnesium aluminium silicate, magnesium silicate, magnesium trisilicate, methoxy PEG-22/dodecyl glycol copolymer, methylcellulose, microcrystalline cellulose, montmorillonite, myristyl alcohol, oat flour, oleyl alcohol, palm kernel alcohol, pectin, PEG-2M, PEG-5M, polyacrylic acid, polyvinyl alcohol, potassium alginate, potassium aluminium polyacrylate, potassium carrageenan, potassium chloride, potassium sulfate, potato starch, propylene glycol alginate, sodium acrylate/vinyl alcohol copolymer, sodium carboxymethyl dextran, sodium carrageenan, sodium cellulose sulfate, sodium chloride, sodium polymethacylate, sodium silicoaluminate, sodium sulfate, stearalkonium bentotnite, stearalkonium hectorite, stearyl alcohol, tallow alcohol, TEA-hydrochloride, tragacanth gum, tridecyl alcohol, tromethamine magnesium aluminium silicate, wheat flour, wheat starch, xanthan gum, abietyl alcohol, acrylinoleic acid, aluminum behenate, aluminum caprylate, aluminum dilinoleate, aluminum salts, such as distearate, and aluminum ?sostearates, beeswax, behenamide, butadiene/acrylonitrile copolymer, C29-70 acid, calcium behenate, calcium stearate, candelilla wax, carnauba, ceresin, cholesterol, cholesterol hydroxystearate, coconut alcohol, copal, diglyceryl stearate malate, dihydroabietyl alcohol, dimethyl lauramine oleate, dodecanoic acid/cetearyl alcohol/glycol copolymer, erucamide, ethylcellulose, glyceryl triacetyl hydroxystearate, glyceryl tri-acetyl ricinolate, glycol dibehenate, glycol di-octanoate, glycol distearate, hexanediol distearate, hydrogenated C6-14 olefin polymers, hydrogenated castor oil, hydrogenated cottonseed oil, hydrogenated lard, hydrogenated menhaden oil, hydrogenated palm kernel glycerides, hydrogenated palm kernel oil, hydrogenated palm oil, hydrogenated polyisobutene, hydrogenated soybean oil, hydrogenated tallow amide, hydrogenated tallow glyceride, hydrogenated vegetable glyceride, hydrogenated vegetable oil, Japan wax, jojoba wax, lanolin alcohol, shea butter, lauramide, methyl dehydroabietate, methyl hydrogenated rosinate, methyl rosinate, methyl styrene/vinyltoluene copolymer, microcrystalline wax, montan acid wax, montan wax, myristyleicosanol, myristyloctadecanol, octadecene/maleic anhyrdine copolymer, octyldodecyl stearoyl stearate, oleamide, oleostearine, ouricury wax, oxidized polyethylene, ozokerite, paraffin, pentaerythrityl hydrogenated rosinate, pentaerythrityl tetraoctanoate, pentaerythrityl rosinate, pentaerythrityl tetraabietate, pentaerythrityl tetrabehenate, pentaerythrityl tetraoleate, pentaerythrityl tetrastearate, ophthalmic anhydride/glycerin/glycidyl decanoate copolymer, ophthalmic/trimellitic/glycols copolymer, polybutene, polybutylene terephthalate, polydipentene, polyethylene, polyisobutene, polyisoprene, polyvinyl butyral, polyvinyl laurate, propylene glycol dicaprylate, propylene glycol dicocoate, propylene glycol diisononanoate, propylene glycol dilaurate, propylene glycol dipelargonate, propylene glycol distearate, propylene glycol diundecanoate, PVP/e?consene copolymer, PVP/hexadecene copolymer, rice bran wax, stearlkonium bentonite, stearalkonium hectorite, stearamide, stearamide DEA-distearate, stearamide DIBA-stearate, stearamide MEA-stearate, stearone, stearyl erucamide, stearyl stearate, stearyl stearoyl stearate, synthetic beeswax, synthetic wax, trihydroxystearin, triisononanoin, triiso stearin, tri-isostearyl trilinoleate, trilaurin, trilinoleic acid, trilinolein, trimyristin, triolein, tripalmitin, tristearin, zinc laurate, zinc myristate, zinc neodecanoate, zinc rosinate, and mixtures thereof. The gelling agents used in vehicles may be natural gelling agents such as natural gums, starches, pectins, agar and gelatin. Often, the gelling agents are based on polysaccharides or proteins Examples include but are not limited to guar gum, Xanthum gum, Alginic acid (E400), sodium alginate (E401), potassium alginate (E402), ammonium alginate (E403), calcium alginate (E404, -polysaccharides from brown algae), Agar (E406, a polysaccharide obtained from red seaweeds), Carrageenan (E407, a polysaccharide obtained from red seaweeds), Locust bean gum (E410, a natural gum from the seeds of the Carob tree), Pectin (E440, a polysaccharide obtained from apple or citrus-fruit), and Gelatin (E441, made by partial hydrolysis of animal collagen).

In various non-limiting embodiments of the invention, the strains and compositions used in a personal care product may further comprise a surfactant. The surfactant may be an anionic surfactant, a cationic surfactant, an ampholytic surfactant, or a nonionic surfactant. Examples of nonionic surfactants include polyethoxylates, fatty alcohols (e.g., ceteth-20 (a cetyl ether of polyethylene oxide having an average of about 20 ethylene oxide units) and other "BRIJ"® nonionic surfactants available from ICI Americas, Inc. (Wilmington, Del.)), cocamidopropyl betaine, alkyl phenols, fatty acid esters of sorbitol, sorbitan, or polyoxyethylene sorbitan. Suitable anionic surfactants include ammonium lauryl sulfate and lauryl ether sulfosuccinate. In various non-limiting embodiments of the invention, a personal care product may comprise water.

In various non-limiting embodiments of the invention, the strains and compositions used in a personal care product may further comprise a hydrogel comprising, for example, a compound such as hydroxypropylmethyl cellulose, cationic hydroxyethyl cellulose (U-care polymers), ethyl cellulose, hydroxypropyl cellulose, hydroxymethyl cellulose, carboxy methyl cellulose, polyethylene oxide (polyox resins), and chitosan pyrrolidone carboxylate (Kytomer PC).

The strains and compositions of the invention are also meant for use in oral health applications. Accordingly, in one particular embodiment, the personal care product is an oral care product, comprising the strains or compositions of the present invention, together with pharmaceutically excipients, or cosmetically acceptable excipients, or other edible ingredients. It is understood that the compositions of the present invention will be in an effective amount. The term "oral care product" refers to products used for keeping the mouth and teeth clean to prevent dental problems, most commonly, dental cavities, gingivitis, periodontal (gum) diseases and bad breath. In this sense, the oral hygiene product is not intentionally swallowed for systemic administration of particular therapeutic agents, but instead is retained in the oral cavity for a time sufficient to contact substantially all of the dental surfaces and/or oral tissues for purposes of oral activity. Non limiting examples of such products are toothpastes, dentifrices, tooth powders, topical oral gels, mouth rinses, denture products, mouth sprays, chewing gums, dental floss, dental tapes, blasting powder, polishing pastes, dental varnishes, fissure sealants, filling materials, oral cream or gel, candy, lozenges, oral dispersible tablet or strip, or powder that may be sprinkled directly into the oral cavity.

In a particular embodiment, the oral care product is selected from the group consisting of a toothpaste, oral gel, oral spray, mouth rinse or oral dispersible tablet.

The oral care products may additionally comprise flavoring and taste-masking agents. Non-limiting examples of these agents for use in oral care products include cinnamic aldehyde, eugenol, eucalyptol, menthol, N-ethyl-p-menthane-3-carboxamide, anethole, peppermint oil, spearmint oil and corn mint oil.

The oral care products may optionally include humectants, gelling agents, abrasives, fluoride sources, desensitizing agents, flavorings, colorings, sweeteners, preservatives, structuring agents, surfactants, anti-calculus agents and anti-plaque agents.

The oral care products may also comprise other orally active agents, such as teeth whitening actives, including bleaching or oxidizing agents like peroxides, perborates, percarbonates, peroxyacids, persulfates, metal chlorites, and combinations thereof. Teeth colour modifying substances may also be considered among the oral care actives useful in the present invention.

The formulation of toothpastes is well-known by those skilled in the art. In the toothpaste compositions, it is preferable to use nonionic (e.g. fatty acids esters with sugars) or amphoteric (e.g. coco-derived betaines) surfactants, since anionic surfactants have a negative effect on the delicate epithelial tissue of the gums. In the case of toothpastes, the use of sodium bicarbonate to neutralize oral acidity is also particularly preferred. In addition, toothpastes can contain thickening agents such as xanthan gum, abrasive silica fillers, and other supplementary agents in addition to those normally used in the toothpaste industry. Preferably, the lactic acid bacteria is encapsulated or protected in other form to be introduced in a toothpaste.

As known by those skilled in the art "mouthwash", "mouthrinse", "dental rinse", "oral rinse" or "mouth bath" as used herein refers to a liquid composition which is held in the mouth passively or swilled around the mouth by contraction of the perioral muscles and/or movement of the head, and may be gargled, where the head is tilted back and the liquid bubbled at the back of the mouth. Usually mouthwashes are an antiseptic solution intended to reduce the microbial load in the oral cavity, although other mouthwashes might be given for other reasons such as for their analgesic, anti-inflammatory or anti-fungal action. Additionally, some rinses act as saliva substitutes to neutralize acid and keep the mouth moist in xerostomia (dry mouth). In addition to water, polyhydroxylated compounds such as glycerine or glycols (e.g., propylene glycol, nonionic surfactants, etc.) and other additives to improve appearance, flavour, and preservation can be included.

The sprays are compositions equal or similar to mouthwashes but dispensed in spray bottles for convenient application of the dose needed to moisten and protect the mouth without requiring subsequent rinsing.

Oral gels include polymers which allows direct, stable application to the oral cavity. In relation to these polymers, for the purposes of this invention it is preferable to use a combination of polymers generically known as polycarbophil and carbomer, since they keep the gel structure stable for very prolonged times under extreme temperature conditions. The gels can also include a quantity of a natural, noncariogenic sweetener, such as sorbitol.

In another embodiment, the personal care product is a cosmetic product, that comprises the *Pediococcus* strains or compositions of the present inventions together with cosmetically acceptable excipients. "Cosmetics products" or "cosmetics" are products intended to be applied to the human body for cleansing, beautifying, promoting attractiveness, or altering the appearance without affecting the body's structure or functions. Cosmetics may also have therapeutical benefits.

The term "cosmetically acceptable" refers to compounds, materials, compositions, and/or dosage forms which are, within the scope of sound medical judgement, suitable for use in contact with human skin without undue toxicity, incompatibility, instability and allergic response, among others. Each "cosmetically acceptable" carrier, excipient, etc., must also be "acceptable" in the sense of being compatible with the other ingredients of the cosmetic formulation. Suitable carriers, excipients, etc. for cosmetic formulations can be found in standard texts.

Non-limiting examples of cosmetic products include cleansing pads, colognes, cotton swabs, cotton pads, eye liner, facial tissue, hair clippers, lip gloss, lipstick, lotion, make-up, nail files, pomade, perfumes, razors, shaving cream, moisturizer, talcum powder, toilet paper and wet wipes (including but not limited to liquid or powder foundation, liquid or solid eyeliner, mascara, cream eye shadow, tinted powder, "pancake" type powder to be used dry or moistened, etc.).

Pharmaceutical Products and Food Supplements

In one aspect, the *Pediococcus* strains and compositions of the present invention are formulated as pharmaceutical products. The term "pharmaceutical product" is understood in its widely meaning in this description, including any composition that comprises an active ingredient, in this case, the strains of the invention preferably in form of composition and optionally at least one antiseptic, together with pharmaceutically acceptable excipients. This term is not limited to medicaments.

The term "pharmaceutically acceptable" is art-recognized, and includes to compounds, materials, compositions, carriers, vehicles and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. Suitable carriers, excipients, etc. can be found in standard pharmaceutical texts. Some non-limiting examples of materials which may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; cocoa butter and suppository waxes; oils, such as peanut oil, cottonseed oil, sunflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Excipients are selected, without limitation, from the group comprising: fillers/diluents/bulking agents, binders, antiadherents, disintegrants, coatings, anti-caking agents, antioxidants, lubricants, sweeteners, flavors, colours, tensides and other classes of pharmaceutically and veterinary acceptable excipients.

Fillers are selected, without limitation, from the group comprising: inulin, oligofructose, pectin, modified pectins, microcrystalline cellulose, lactose, starch, maltodextrin, saccharose, glucose, fructose, mannitol, xylitol, non-crystallizing sorbitol, calcium carbonate, dicalcium phosphate, other inert inorganic and organic pharmacologically acceptable fillers, and mixtures of these substances. At dosage form of oral suspension, fillers or diluents are selected from the group comprising: vegetable oil, oleic acid, oleyl alcohol, liquid polyethylene glycol, other pharmacologically acceptable inert liquids, or mixtures of these substances.

Binders are used in solid dosage forms, e.g. to hold the ingredients in a tablet together, to ensure that tablets and granules can be formed with required mechanical strength, and to give volume to low active dose tablets. Binders in solid dosage forms like tablets are: lactose, sucrose, corn (maize) starch, modified starches, microcrystalline cellulose, modified cellulose (for example hydroxypropyl methylcellulose (HPMC) and hydroxyethylcellulose), other water soluble cellulose ethers, polyvinylpyrrolidone (PVP) also known as povidone, polyethylene glycol, sorbitol, maltitol, xylitol and dibasic calcium phosphate; other suitable pharmacologically acceptable binders, or mixtures of these substances.

Antiadherents are used to reduce the adhesion between the powder (granules) and the punch faces and thus prevent sticking to tablet punches. They are also used to help protect tablets from sticking. The most commonly used is magnesium stearate.

As disintegrants and superdisintegrants in solid dosage forms like tablets and capsules, the following substances, without limitation, are used: cross-linked polyvinylpyrrolidone, sodium starch glycolate, sodium carboxymethyl cellulose, calcium carboxymethyl cellulose, and formaldehyde-casein, other suitable pharmacologically acceptable disintegrant and superdisintegrant, or their mixtures.

Coatings in the case of solid dosage forms, such as tablets and granules for capsules filling, protect the ingredients from deterioration by moisture in the air, make large, unpleasant-tasting tablets easier to swallow and/or in the case of enteric coatings ensure intact passage through a strong acidic medium of gastric juice (pH around 1), and which allow release in duodenum or ileum (small intestine). For most coated tablets, a cellulose ether hydroxypropyl methylcellulose (HPMC) film coating is used. Occasionally, other coating materials are used, for example synthetic polymers and co-polymers like polyvinylacetate phthalate (PVAP); co-polymers of methyl acrylate-metacrylic acid; co-polymers of methyl metacrylate-metacrylic acid; shellac, corn protein zein or other polysaccharides; waxes or wax-like substances such as beeswax, stearic acid; higher fatty alcohols like cetyl or stearyl alcohol; solid paraffin; glycerol monostearate; glycerol distearate, or their combinations. Capsules are coated with gelatin or hydroxypropyl methylcellulose.

Enteric coatings control the rate of drug release and determine where the drug will be released in the digestive tract. Materials used for enteric coatings include fatty acids, waxes, shellac, plastics, and plant fibers and their mixtures, also in combination with other above mentioned coatings.

An anticaking agent is an additive placed in powdered or granulated materials to prevent the formation of lumps (caking) and for easing packaging, transport, and consumption. As anti-caking agents in solid dosage forms like tablets, capsules, or powders, the following are used: magnesium stearate, colloidal silicon dioxide, talc, other pharmacologically acceptable anticaking agents, or their mixtures.

Lubricants are used in solid dosage forms, in particular in tablets and capsules, to prevent ingredients from clumping together and from sticking to the tablet punches or capsule filling machine, and also in hard capsules. As lubricants talc or silica, and fats, e.g. vegetable stearin, magnesium stearate or stearic acid, and mixtures thereof, are the most frequently used lubricants in tablets or hard gelatin capsules.

Sweeteners are added to make the ingredients more palatable, especially in solid dosage forms, e.g. chewable tablets, as well as in liquids dosage forms, like cough syrup. Sweeteners may be selected from artificial, natural or synthetic or semi-synthetic sweeteners; non-limiting examples of sweeteners are aspartame, acesulfame potassium, cyclamate, sucralose, saccharine, sugars or any mixture thereof, Flavors can be used to mask unpleasant tasting active ingredients in any dosage form. Flavorings may be natural (e.g. fruit extract) or artificial. For example, to improve: (1) a bitter product, mint, cherry or anise may be used; (2) a salty product, peach or apricot or liquorice may be used; (3) a sour product, raspberry; and (4) an excessively sweet product, vanilla.

Except auxiliary substances from the class of excipients, the formulation from the present invention can contain other pharmacologically active or nutritive substances including, but not limited, to vitamins, such as vitamin D (calciferol) in the pharmaceutically acceptable chemical form, salt or derivatives; minerals in the form of pharmaceutically and nutritive acceptable chemical form; and L-amino acids. Regarding the preparation of the formulations of the present invention is within the scope of ordinary person skilled in the art and will depend upon the final dosage formulation. For instance, and without limitation, when the final dosage forms is an oral solid one, such as tablets, capsules, powder, granules, oral suspension, etc. the process for preparation of solid dosage forms of the formulation includes homogenization of: (1) the active ingredient(s), comprising at least one or more post-treated probiotic bacteria of the invention in an effective amount; (2) with one or more excipients to form homogeneous mixture which is, e.g. according to requirements, subjected to lubrication with magnesium stearate or other lubricants yielding final dosage form of powder. Such homogeneous powder is filled into ordinary gelatin capsules or, alternatively, into gastro-resistant capsules. In the case of tablets, they are manufactured by direct compression or granulation. In the first case, a homogeneous mixture of active ingredients and suitable excipients such as anhydrous lactose, non-crystallizing sorbitol, and others is prepared. In the second case, tablets are processed on the mixture in granulated form. Granules are prepared by granulation process of active ingredients of the formulation with suitable fillers, binders, disintegrants, and small amount of purified water. Such prepared granules are sieved and dried until the water content of <1% w/w.

Regarding the process for preparation of liquid dosage forms (e.g. oral suspension), it involves homogenization of the active ingredient(s) of the formulation comprising at least one or more post-treated probiotic bacteria of the invention in an effective amount in an inert liquid diluent (filler) such as various vegetable oils like sunflower, soybean or olive oil; oleic acid; oleyl alcohol; liquid polyethylene glycols like PEG 200, PEG 400 or PEG 600; or other inert pharmacologically acceptable liquids. The process further involves treatment of homogeneous mixture with one or more processes selected from the group comprising: (1) stabilization of the formulation, by addition and homogenization of suspension stabilizers like beeswax, colloidal silicon dioxide, etc.; (2) sweetening of the formulation; by addition and homogenization of sweetener; (3) flavoring of the formulation, by addition and homogenization of flavoring. Such forms of the formulation can contain also other excipients or ingredients, usually employed in the art.

The pharmaceutical product can adopt different forms or names depending on the product approval route and also depending on the country. For instance, a medicament is a particular pharmaceutical product. A medical food is another particular pharmaceutical product. The terms "medical food" or "food for special medical purposes" are used in some countries to refer to a food specially formulated and intended for the dietary management of a disease that has distinctive nutritional needs that cannot be met by normal diet alone. They are defined in regulations such as the Food and Drug Administration's 1988 Orphan Drug Act Amendments in the United States, and the Commission Directive 1999/21/EC in Europe. Medical foods are distinct from the broader category of food supplements and from traditional foods that bear a health claim. Thus, in a particular embodiment, the strains of the invention are formulated as a medical food.

Often, *Pediococcus* strains and compositions such as the one disclosed herein, are considered as food supplements. A food supplement, also known as dietary supplement or nutritional supplement is considered another particular pharmaceutical product. This is a preparation or product intended to supplement the diet, made from compounds usually used in foodstuffs, which provide nutrients or beneficial ingredients that are not usually ingested in the normal diet or may not be consumed in sufficient quantities. Mostly, food supplements are considered as food products, but sometimes they are defined as drugs, natural health products, or nutraceutical products. In the sense of the present invention, food supplements also include nutraceuticals. Food supplements are usually sold "over the counter", i.e. without prescription. If the food supplement adopts the form of a pill, a capsule a tablet or a powder, it comprises excipients which are the same as the used in medicaments. A food supplement however, can also adopt the form of a food product which is fortified with some nutrients (e.g. a bar or yoghurt). Thus, in a particular embodiment, the strains of the invention are formulated as a food supplement. The food supplement can be administered as such, can be mixed with a suitable drinkable liquid, such as water, yoghurt, milk or fruit juice, or can be mixed with solid or liquid food. In this context the food supplement can be in the form of tablets or lozenges, pills, capsules, granules, powders, suspensions, sachets, sweets, bars, syrups and corresponding administration forms, usually in the form of a unit dose.

The strains of the invention can be also included in a variety of food products, such as a milk products (a yogurt, a cheese, a fermented milk, a milk powder, a milk based fermented product, an ice-cream, a fermented cereal based product, a milk based powder), bread, bars, spreads, biscuits and cereals, a beverage, different types of oil, or a dressing. The term "food product" is used herein in its broadest meaning, including any type of product, in any form of presentation, which can be ingested by an animal, but excluding pharmaceutical and veterinary products. Examples of other food products are meat products, chocolate spreads, fillings and frostings, chocolate, confectionery, baked goods, sauces and soups, fruit juices and coffee whiteners. Particularly interesting food products are food supplements and infant formulas. The food product preferably comprises a carrier material such as oat meal gruel, lactic acid fermented foods, resistant starch, dietary fibres, carbohydrates, proteins and glycosylated proteins. In a particular embodiment the strains of the invention are encapsulated or coated.

Another aspect of the present invention relates to a solid composition comprising a cryoprotectant; a freeze-dried biomass comprising at least one lactic acid bacteria of the invention; and a pharmaceutically acceptable carrier. The pharmaceutically acceptable carrier preferably is chosen from an emulsion, a gel, a paste, granules, a powder, and a gum. Additional aspects of the invention provide an oral care product, a pharmaceutical composition, and edible product, a dietary supplement and a cosmetic composition comprising an effective amount of the composition as defined in the previous aspect. In a particular embodiment, the oral care product is a chewing gum, a tooth paste, a mouth spray, a lozenge, or an oral dispersible tablet. In a particular embodiment, the pharmaceutical composition, the edible product or the dietary supplement, is a lozenge or an oral dispersible tablet.

Medical Applications and Methods of Use

An aspect of the invention relates to the *Pediococcus* strains and compositions of the invention for use as medicaments. This aspect can alternatively be formulated as a method for probiotic treatment, comprising administering in a need thereof an effective amount of a composition comprising at least one isolated strain of lactic acid bacteria as defined in the first aspect of the present invention. The term "probiotic" as used herein, refers to live microorganisms that, when administered in adequate amounts, confer a health benefit on the host.

Specifically, in exerting several beneficial effects in the human host, the strains of the present invention are useful for treating diseases or conditions related with dysbiosis or caused by pathogens. Dysbiosis (also called dysbacteriosis), as used herein, is a term for a microbial imbalance or maladaptation on or inside the body, such as an impaired microbiota. For example, a part of the human microbiota, such as the skin flora, gut flora, vaginal flora, oral can become deranged, with normally commensal dominating species underrepresented and normally outcompeted or contained species increasing to fill the void. A loss of beneficial microbes, expansion of pathobionts, and loss of diversity are events that encompass dysbiosis. Dysbiosis may be caused by such diverse things as repeated and inappropriate antibiotic or antiseptic exposure. Thus, one aspect of the invention is the strains of the invention, useful in combination with antiseptics, for use in the prevention and/or treatment of dysbiosis or of conditions associated to a dysbiosis.

Another aspect relates to the compositions of the invention for use in the prevention and/or treatment of dysbiosis or of conditions associated to a dysbiosis.

The strains of the invention are particularly useful in the dental hygiene. Thus, in one aspect, the invention provides the compositions and the strains of the invention for use in combination with antiseptics, for use in the prevention and/or treatment of a disorder in the oral cavity of an animal, including a human. Alternatively, this aspect can be formulated as the use of the strains or compositions of the invention for the manufacture of a medicament for the prevention and/or treatment of a disorder in the oral cavity of an animal, including a human. Also alternatively, the invention also provides a method for the prevention and/or treatment of a disorder in the oral cavity of an animal, including a human, comprising administering to said animal in need thereof the strains or compositions as defined in the invention.

Particularly, the disorder in the oral cavity is caused by oral pathogens. Illustrative non-limitative examples of "disorder from the oral cavity which is caused by an oral pathogen" are plaque-related diseases, caries, gingivitis, periodontitis, candidiasis, herpes and ulcers, as well as halitosis, stained teeth, sensitive teeth, peri-implant diseases, among others.

In one embodiment, the *Pediococcus* strains and compositions thereof are used for the treatment and/or prevention of periodontal diseases, including, but not limited to gingivitis, periodontitis and peri-implant diseases. Particularly, the periodontal disease is gingivitis or periodontitis.

In a further embodiment, the *Pediococcus* strains and compositions are used for the treatment and/or prevention of candidiasis.

Periodontal therapy is typically first removing mechanically the subgingival plaque by scraping or by ultrasound; by this mechanical removal, the bacteria in the biofilm are released and flushed out. In the course of this treatment, antiseptic compositions are used today, which are designed to prevent the re-colonization by gram-negative bacteria. The disadvantage of a regular and extensive use of compositions containing antiseptics, however, is the side effects of these products and the harmful effect on commensal microbiota.

In another embodiment, the strains and compositions of the present invention are useful for treating skin disorders. Examples of skin disorders include, but are not limited to nail fungal infections; superficial skin disorders (e.g., erysipelas, open-wound infections, acne, abscess, boil, eczema, dermatitis, contact dermatitis, hyper-sensitinitis, contact lesions, bed sores, and diabetic lesions).

Methods of screening One aspect of the present invention provides a method for screening and isolating a lactic acid bacteria strains, comprising the following steps:

i) assaying the ability to tolerate antiseptics of individuals of lactic acid bacteria from a pool of lactic acid bacteria strain candidates; and ii) selecting and isolating the lactic acid bacteria strains with an ability to tolerate antiseptics higher than that of *Porphyromonas gingivalis*.

In one embodiment, the ability to tolerate antiseptics is expressed as inhibition halo determined by a disc diffusion assay.

In one particular embodiment, the ability to tolerate antiseptics, comprises the following steps:

i) swabbing uniformly a suspension of the lactic acid bacteria in phosphate buffered saline 0.1M with optical density equivalent to a Mc Farland standard No. 3 on nutrient medium in a plate to obtain a confluent layer;

ii) placing a cellulose disc of 6 mm diameter in contact with the nutrient medium;

iii) adding the antiseptic to the cellulose disc in concentration that inhibits the growth of *Porphyromonas gingivalis*;

iv) incubating overnight at 37° C. under anaerobic or microaerophilic conditions;

v) measuring in millimeters the inhibitions zones after 24 or 48 hours by placing the plate over a flat rule;

vi) expressing the results as inhibition halo.

The skilled in the art is routinely able to select the nutrient medium of steps i)-ii) according to the nutritional requirements of the lactic bacteria strain to be tested.

In one embodiment, the method for screening and isolating lactic acid bacteria is used for screening and isolating a lactic acid bacteria strain for personal care. In a particular embodiment the method is for screening and isolating a lactic acid bacteria for oral care.

In one embodiment, the pool of lactic acid bacteria strain candidates used for assaying the ability to tolerate antiseptics comprises lactic acid bacteria strains of *Lactobacillus* or *Pediococcus* genus. Particularly, the strain candidates are *Pediococcus* strains, more particularly, *Pediococcus acidilactici* strains.

EXAMPLES

Figure 1:
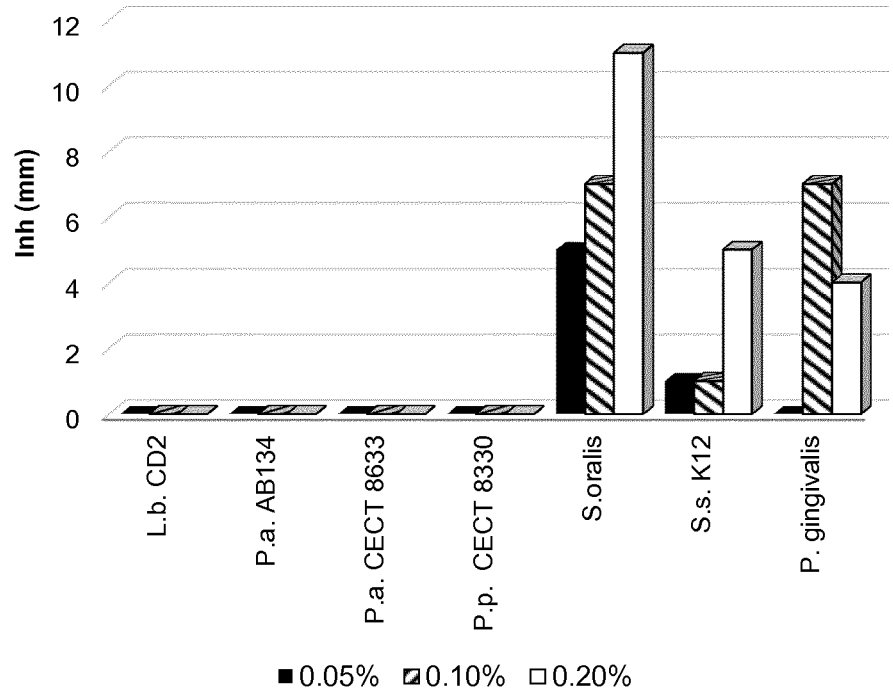
FIG. 1. Tolerance of bacteria to triclosan expressed as inhibition halo (Inh) in millimeters (mm) determined by disc diffusion assay. *Lactobacillus brevis* CD2 (L.b. CD2); *Pediococcus acidilactici* AB134 (P.a. AB134); *Pediococcus acidilactici* CECT 8633 (P.a. CECT 8633); *Pediococcus pentosaceus* CECT 8330 (P.p. CECT8330); *Streptococcus oralis; Streptococcus salivarius* K12 (S.s. K12); and *Porphyromonas gingivalis*.

Example 1. Isolation and Identification of *Pediococcus acidilactici* CECT8633

Lactic acid bacteria candidates were isolated from fresh stools from 0-9 year-old children. Samples were dissolved in PBS buffer (pH 7.4), aliquoted and plated on MRS supplemented with various antibiotic combinations. Strains were cultured under microaerophilic conditions (5% $CO_2$) at 37 or 30° C. Incubation time depended on the growth rate, but ran normally from 24 hours to 3 days. Isolation of individual strains proceeded with the same selection media, and then Gram staining was carried out in order to get a first identification. Once grown, isolated strains were stored by freeze-drying in PBS 0.1× with 15% skim milk powder.

Identification at species level was performed by sequencing 16S rRNA gene. Bacteria were grown overnight on MRS medium (pH 6.4) at 37° C. in an atmosphere containing 5% $CO_2$. Bacteria were further harvested, washed and resuspended in pre-lysis buffer (480 μl EDTA 50 mM pH 8.0; 120 μl lysozyme 10 mg/ml), and further incubated at 37° C. for 60 min. DNA was extracted using Wizard genomic DNA purification kit (Promega). After centrifugation of the pre-treated bacteria at 14000 g for 2 min to remove the supernatant, the Promega's protocol was followed. In brief, bacteria were resuspended in Nuclei Lysis Solution and incubated at 80° C. for 5 min, then cooled to room temperature. Cell lysates were incubated in RNase solution at 37° C. for 60 min and proteins were precipitated by adding the Protein Precipitation Solution and vortexing at high speed. Samples were cooled down and centrifuged at 15000 g for 3 min. The supernatants containing the DNA were transferred to clean 1.5 ml microfuge tubes and mixed with 600 μl of isopropanol by inversion. DNA was collected by centrifugation at 15000 g for 2 min and carefully pouring off the supernatant. DNA samples were washed with 600 μl of 70% ethanol by gently inverting the tube several times. Ethanol was removed by aspiration, after centrifugation at 15000 g for 2 min. Finally, the DNA pellet was resuspended in 100 μl of Rehydration Solution by incubating at 65° C. for 1 h. Samples were stored at 2-8° C.

The 16S rRNA was amplified by PCR using the universal primers for eubacteria Eub27f and Eub1492r. Then, the DNA obtained as explained above was washed using the kit Quiaquick (Quiagene). Four consecutive sequencing reactions were performed for each sample in a Genetic Analyzer 3130 (Applied Biosystems) using BigDye kit v.3.1, using the primers 27F, 357F, 907R and 1492R. Data collection and chromatograms were built using DNA Sequence Analysis v.5.2 software (Applied Biosystems) and checked by visual analysis with Chromas (Technelysium Pty Ltd.) and BioEdit (Ibis Biosciences).

Genus Identification was carried out using the Ribosomal Database Project tool and Species identification was performed by comparison of the obtained sequence with 16S sequences of known organisms from both RefSeq data base (http://www.ncbi.nlm.nih.gov/RefSeq/) by means of a BLASTN, and from Ribosomal Database Project (http://rdp.cme.msu.edu/)).

The strain CECT8633 was identified as *Pediococcus acidilactici* and deposited in the Spanish Type Culture Collection (Universitat de Valencia, Campus de Burjassot, Edif. de Investigación, 46100 Burjassot, Valencia, Spain) on 26 May 2014. The deposited is viable and keeps all their features related to their deposit.

The 16S rRNA sequence obtained for strain CECT8633 corresponds to SEQ ID NO: 1.

Example 2. Tolerance of Lactic Acid Bacteria Strains to Antiseptics (Disc Diffusion Assay)

LAB strains with presumed probiotic properties namely *L. brevis, P. acidilactici, P. pentosaceus, S. oralis* and *S. salivarius* were seeded in agar plates with the appropriate nutrient media and incubated in order to obtain isolated colonies. *Porphyromonas gingivalis* DSM20709 was used as an example of pathogens associated with periodontal pathologies. For each strain the nutritive media and atmospheric conditions used were the most suitable for their proper growth as summarized in TABLE 1.

TABLE 1

Nutrient media and growth conditions for assayed bacteria

| Strain | Medium | $T^a$ | Time (h) | Atmosphere |
|---|---|---|---|---|
| *L. brevis* CD2 | MRS | 37° C. | 24 h | 5% $CO_2$ |
| *P. acidilactici* CECT8633 | MRS | 37° C. | 24 h | 5% $CO_2$ |
| *P. acidilactici* AB134 | MRS | 37° C. | 24 h | 5% $CO_2$ |
| *P. pentosaceus* CECT8330 | MRS | 37° C. | 24 h | 5% $CO_2$ |
| *S. oralis* | BHI | 37° C. | 24 h | 5% $CO_2$ |
| *S. salivarius* K12 | BHI | 37° C. | 24 h | 5% $CO_2$ |
| *P. gingivalis* | Sheep Blood Agar | 37° C. | 48 h | Anaerobiosis |

For each microorganism, isolated colonies were used for preparing a suspension in Phosphate Buffered Saline 0.1M (PBS) with an optical density equivalent to a Mc Farland standard No. 3. The suspension was used for obtaining a confluent layer of microorganism over the corresponding nutrient medium (TABLE 1) by uniformly seeding the microorganism using a sterile swab.

Immediately after the inoculation of the strains in the plates, 6 mm of cellulose discs were placed. The discs were impregnated with different conventional antiseptics according to TABLE 2:

TABLE 2

Antiseptics used for the study of lactic acid bacteria tolerance.

| Mouthwash antiseptic | Solvent | Volume | Concentration (% in v/v or mg/mL) | | |
|---|---|---|---|---|---|
| Chlorexidine | Dimethyl-formamide | 5 uL | 0.12% | 0.06% | 0.03% |
| Chlorexidine gluconate | PBS | 20 uL | 0.12% | 0.06% | 0.03% |
| Triclosan | EtOH | 5 uL | 0.2% | 0.1% | 0.05% |
| Listerine Zero ® | PBS | 20 uL | — | Dil. 1:2 | Dil. 1:4 |
| Listerine Original ® | PBS | 20 uL | — | Dil. 1:2 | Dil. 1:4 |
| Thymol | EtOH | 5 uL | 1.2 mg/mL | 0.6 mg/mL | 0.3 mg/mL |

The volume used was the maximum allowed by the disc without spreading on the medium. The solvent was confirmed to not be inhibitory against the bacteria at the amount used. Microorganism were allowed to grow according to the conditions of TABLE 1, and halos of inhibition (in millimeters) measured after 24 h or 48 h according to the corresponding optimal growth conditions for the microorganisms. Results were obtained in triplicate.

Figure 2:
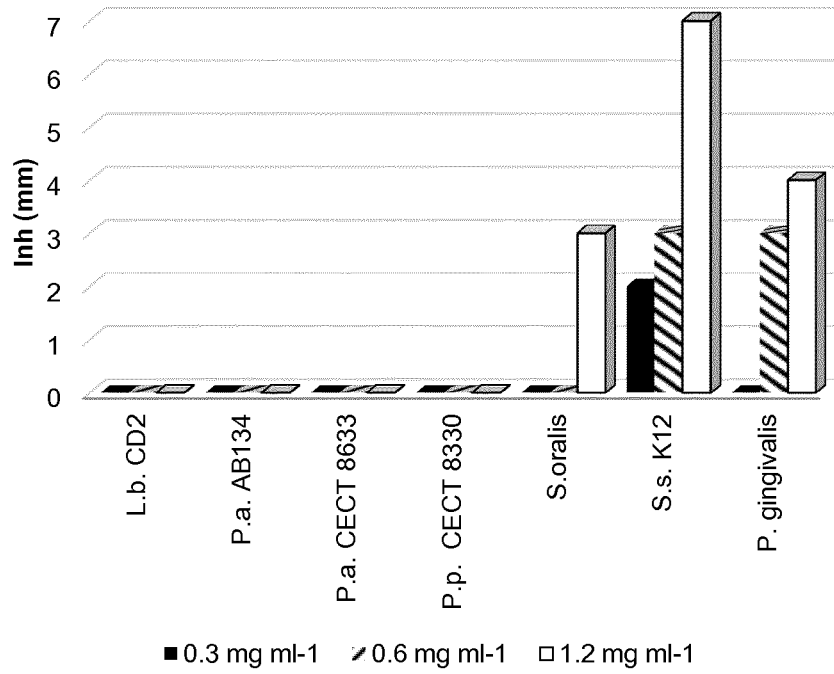
FIG. 2. Tolerance of bacteria to thymol expressed as inhibition halo (Inh) in millimeters (mm) determined by disc diffusion assay. *Lactobacillus brevis* CD2 (L.b. CD2); *Pediococcus acidilactici* AB134 (P.a. AB134); *Pediococcus acidilactici* CECT 8633 (P.a. CECT 8633); *Pediococcus pentosaceus* CECT 8330 (P.p. CECT8330); *Streptococcus oralis; Streptococcus salivarius* K12 (S.s. K12); and *Porphyromonas gingivalis*.
Figure 3:
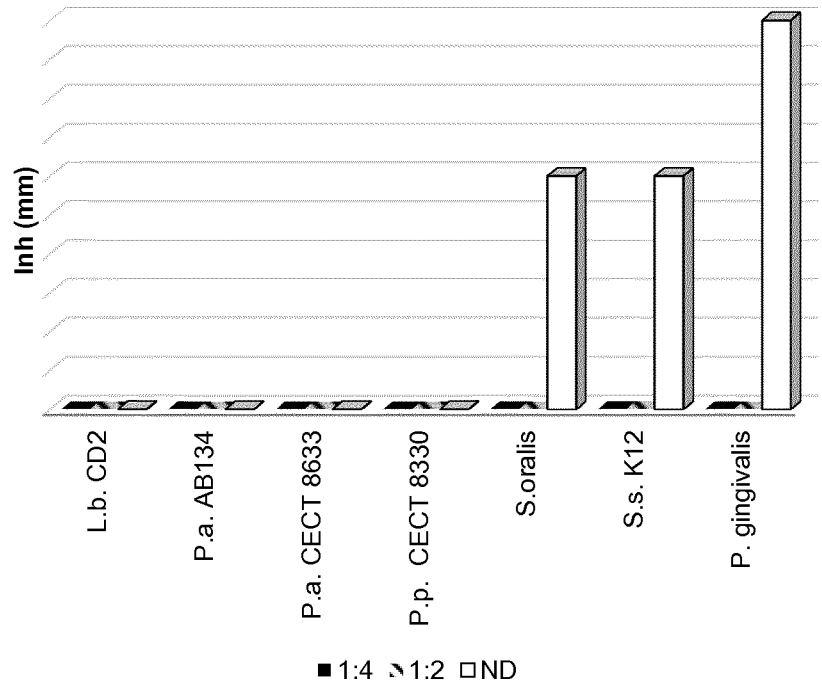
FIG. 3. Tolerance of bacteria to Listerine Original® expressed as inhibition halo (Inh) in millimeters (mm) determined by disc diffusion assay. *Lactobacillus brevis* CD2 (L.b. CD2); *Pediococcus acidilactici* AB134 (P.a. AB134); *Pediococcus acidilactici* CECT 8633 (P.a. CECT 8633); *Pediococcus pentosaceus* CECT 8330 (P.p. CECT8330); *Streptococcus oralis; Streptococcus salivarius* K12 (S.s. K12); and *Porphyromonas gingivalis*.
Figure 4:
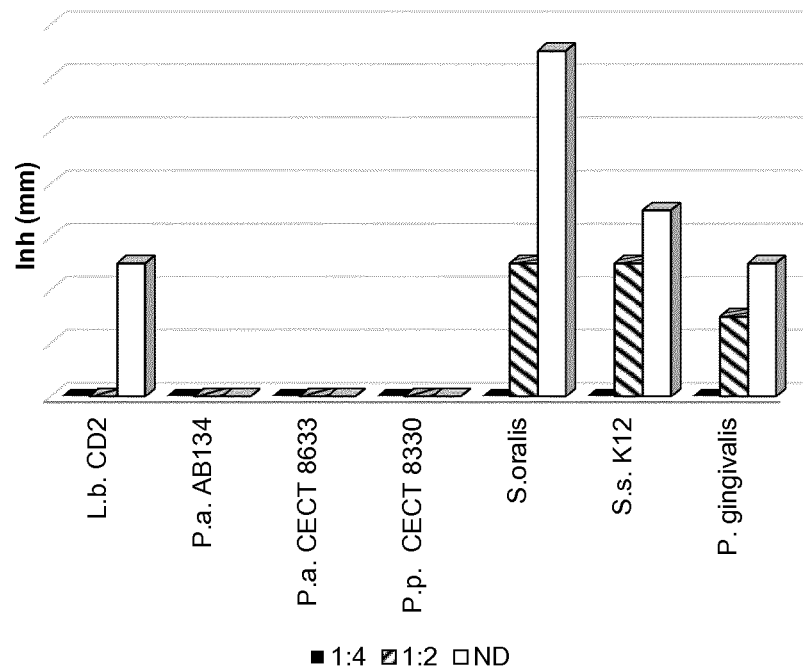
FIG. 4. Tolerance of bacteria to Listerine Zero® expressed as inhibition halo (Inh) in millimeters (mm) determined by disc diffusion assay. *Lactobacillus brevis* CD2 (L.b. CD2); *Pediococcus acidilactici* AB134 (P.a. AB134); *Pediococcus acidilactici* CECT 8633 (P.a. CECT 8633); *Pediococcus pentosaceus* CECT 8330 (P.p. CECT8330); *Streptococcus oralis; Streptococcus salivarius* K12 (S.s. K12); and *Porphyromonas gingivalis*.

FIG. 1 depicts the inhibition observed for each microorganism in the presence of triclosan at different concentrations. The pathogen *P. gingivalis* as well as the *Streptococcus* sp. strains were inhibited by triclosan. However, neither *Lactobacillus brevis* nor the strains belonging to *Pediococcus* genus were inhibited. Similarly, thymol inhibited the growth of *P. gingivalis* and *Streptococcus* sp. strains and the highest concentration tested 1.2 mg/mL, but not *Lactobacillus brevis* or *Pediococcus* strains (FIG. 2). Same effect was observed when discs where impregnated with 20 microliters of Listerine Original® (with alcohol) not diluted (FIG. 3). *P. gingivalis* and *Streptococcus* strains were also inhibited by Listerine Zero® and its corresponding 2-fold dilution (FIG. 4). The tolerance of *L. brevis* to the presence of Listerine Zero® was higher than that of *P. gingivalis* and *Streptococcus* as no inhibition was observed in the presence of 4-fold and 2-fold dilutions of Listerine Zero®. However, in contrast to triclosan, thymol and Listerine Original®, the presence of Listerine Zero® not diluted had an inhibitory effect on *L. brevis*. None of the *Pediococcus* strains were inhibited by the presence of Listerine Zero® as observed for Listerine Original®.

Figure 5:
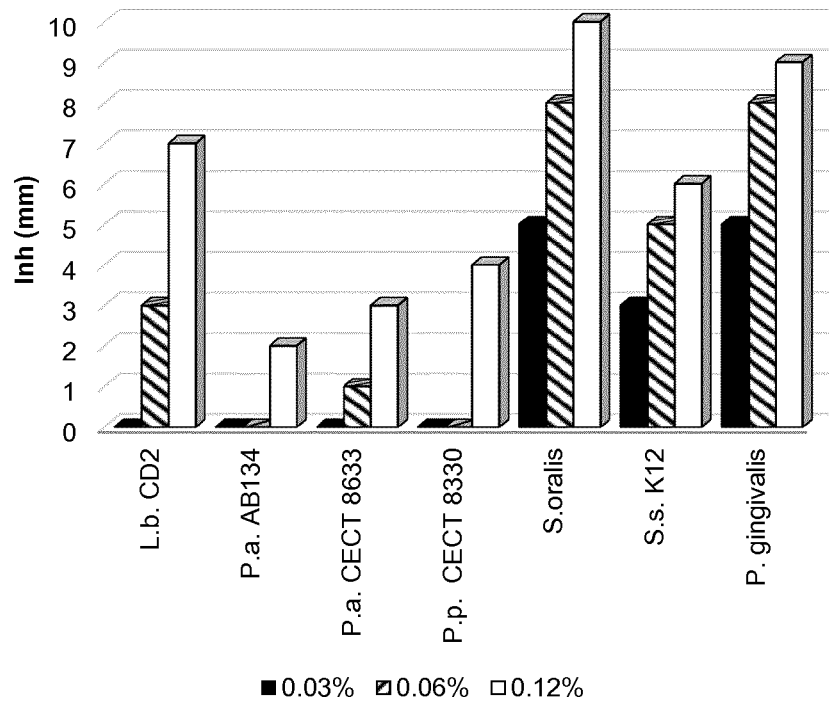
FIG. 5. Tolerance of bacteria to chlorhexidine expressed as inhibition halo (Inh) in millimeters (mm) determined by disc diffusion assay. *Lactobacillus brevis* CD2 (L.b. CD2); *Pediococcus acidilactici* AB134 (P.a. AB134); *Pediococcus acidilactici* CECT 8633 (P.a. CECT 8633); *Pediococcus pentosaceus* CECT 8330 (P.p. CECT8330); *Streptococcus oralis; Streptococcus salivarius* K12 (S.s. K12); and *Porphyromonas gingivalis*.
Figure 6:
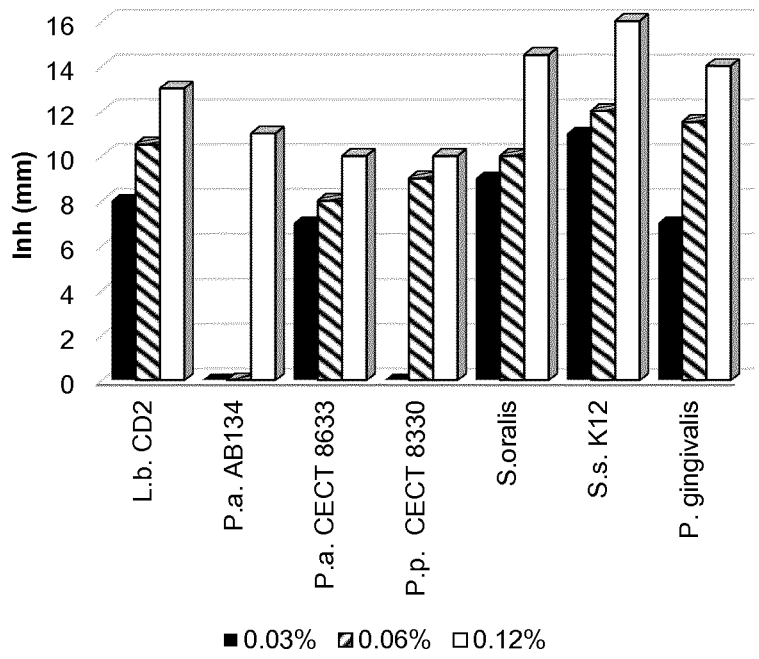
FIG. 6. Tolerance of bacteria to chlorhexidine gluconate expressed as inhibition halo (Inh) in millimeters (mm) determined by disc diffusion assay. *Lactobacillus brevis* CD2 (L.b. CD2); *Pediococcus acidilactici* AB134 (P.a. AB134); *Pediococcus acidilactici* CECT 8633 (P.a. CECT 8633); *Pediococcus pentosaceus* CECT 8330 (P.p. CECT8330); *Streptococcus oralis; Streptococcus salivarius* K12 (S.s. K12); and *Porphyromonas gingivalis*.
Figure 7:
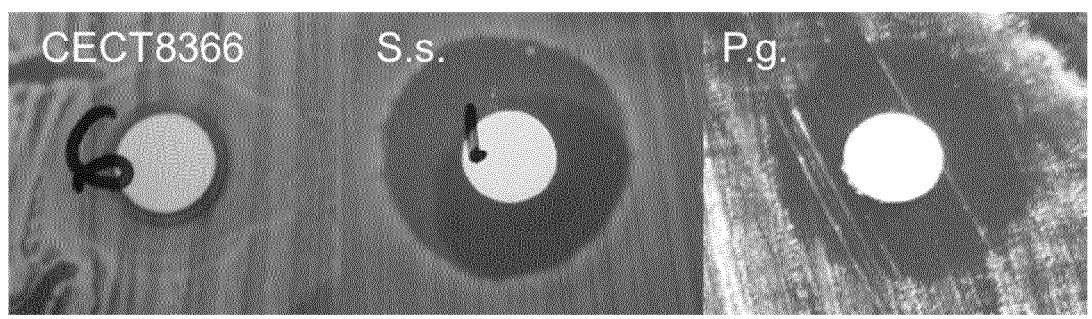
FIG. 7. Halos of inhibition observed for *Pediococcus acidilactici* CECT8633, *Streptococcus salivarius* K12 (S.S.) and *Porphyromonas gingivalis* (P.g.) around 6-mm cellulose discs impregnated with 20 µl of chlorhexidine gluconate 0.12% (v/v).
Figure 8:
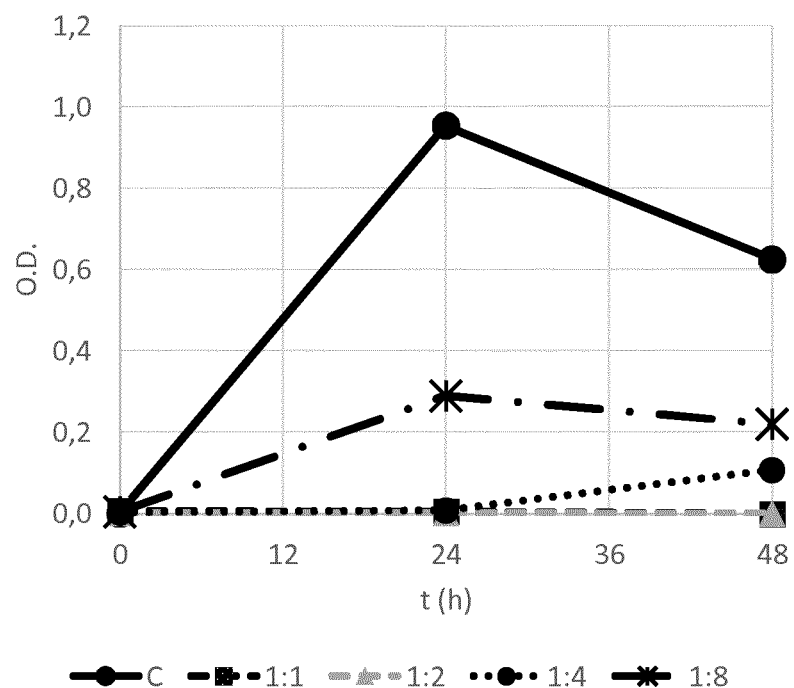
FIG. 8. Growth kinetics of *Streptococcus salivarius* K12 in the absence (control) or presence of different concentrations of Listerine Zero® (C, control without antiseptic; 1:1, not diluted; 1:2, 2-fold dilution; 1:4, 4-fold dilution; 1:8, 8-fold dilution). X-axis=time (t) in hours (h).
Figure 9:
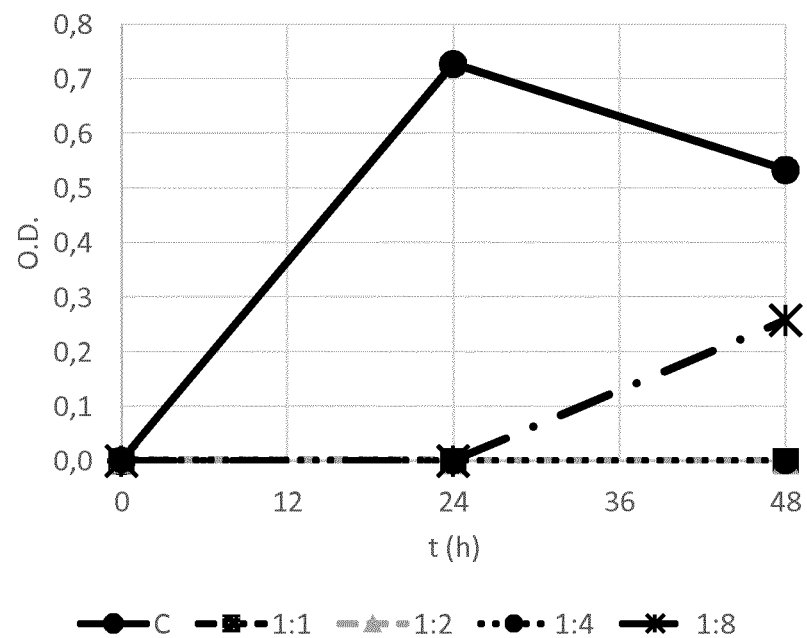
FIG. 9. Growth kinetics of *Streptococcus oralis* in the absence (control) or presence of different concentrations of Listerine Zero® (C, control without antiseptic; 1:1, not diluted; 1:2, 2-fold dilution; 1:4, 4-fold dilution; 1:8, 8-fold dilution). X-axis=time (t) in hours (h).
Figure 10:
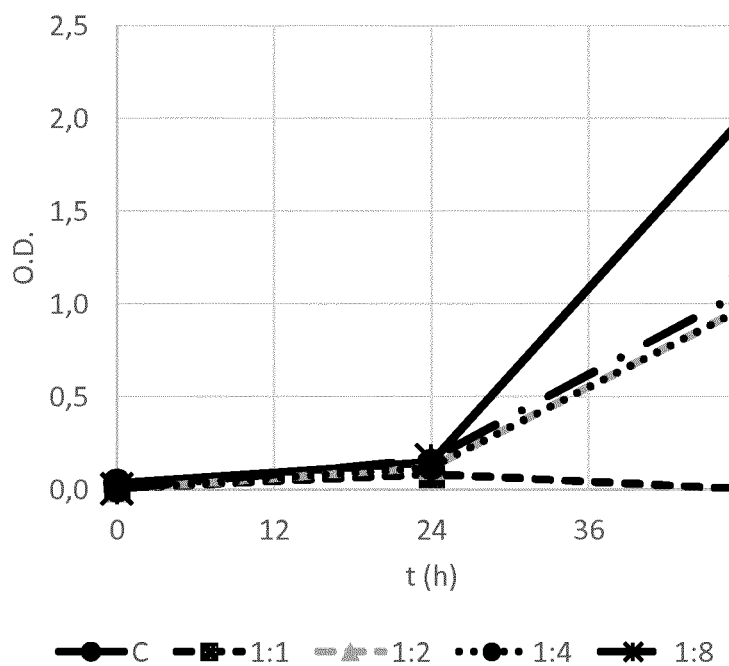
FIG. 10. Growth kinetics of *Lactobacillus brevis* CD2 in the absence (control) or presence of different concentrations of Listerine Zero® (C, control without antiseptic; 1:1, not diluted; 1:2, 2-fold dilution; 1:4, 4-fold dilution; 1:8, 8-fold dilution). X-axis=time (t) in hours (h).
Figure 11:
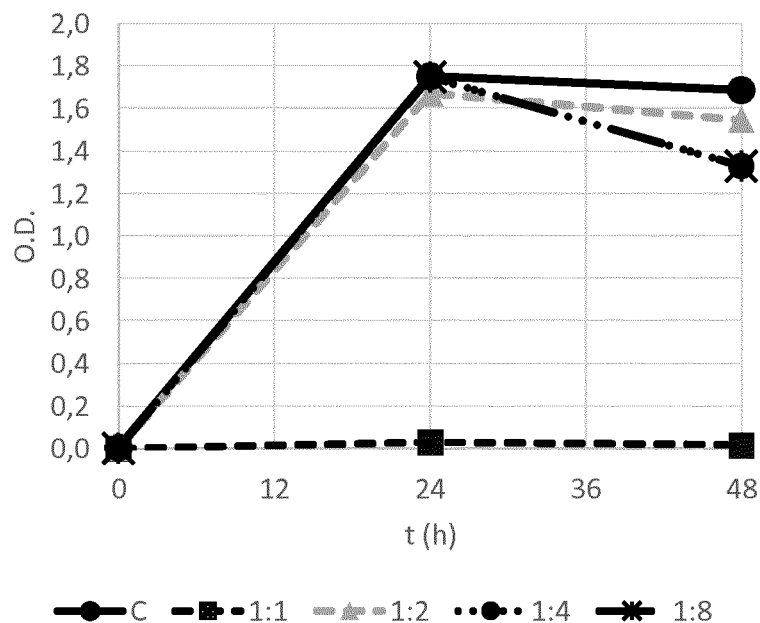
FIG. 11. Growth kinetics of *Pediococcus pentosaceus* CECT8330 in the absence (control) or presence of different concentrations of Listerine Zero® (C, control without antiseptic; 1:1, not diluted; 1:2, 2-fold dilution; 1:4, 4-fold dilution; 1:8, 8-fold dilution). X-axis=time (t) in hours (h).
Figure 12:
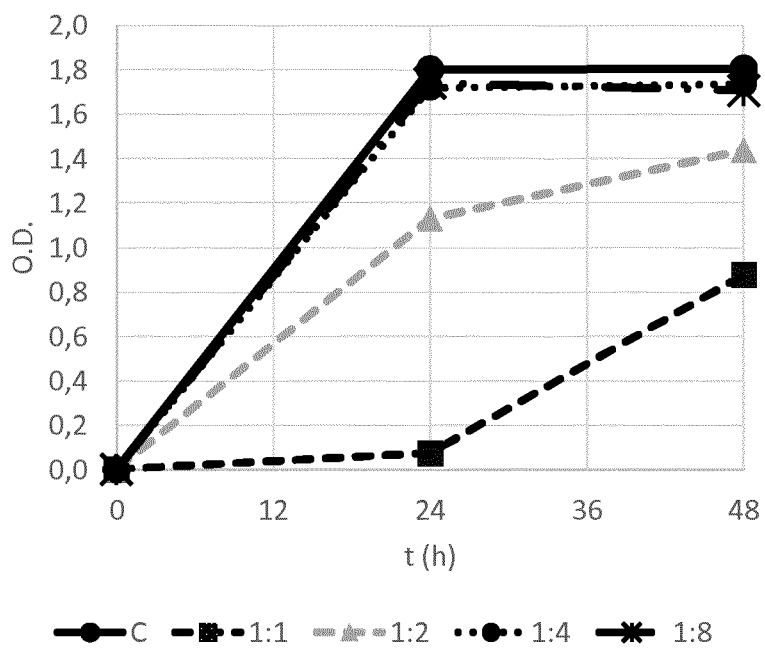
FIG. 12. Growth kinetics of *Pediococcus acidilactici* AB134 in the absence (control) or presence of different concentrations of Listerine Zero® (C, control without antiseptic; 1:1, not diluted; 1:2, 2-fold dilution; 1:4, 4-fold dilution; 1:8, 8-fold dilution). X-axis=time (t) in hours (h).
Figure 13:
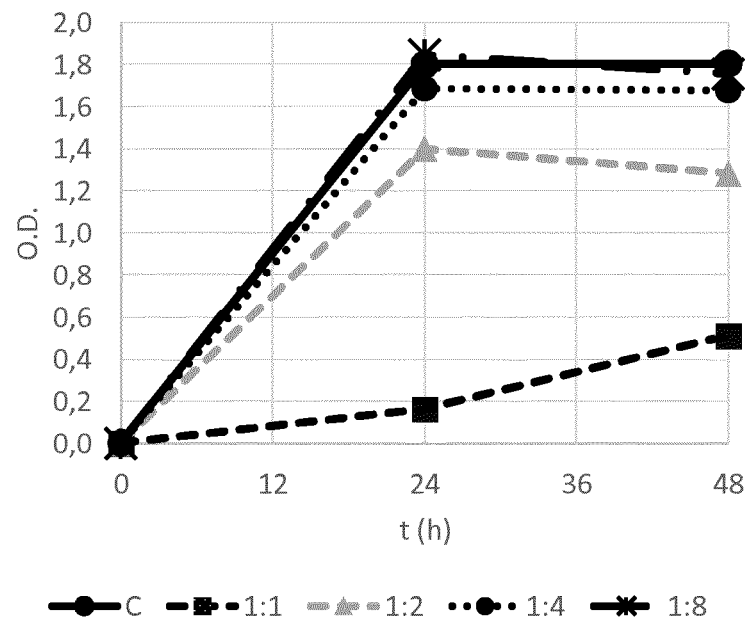
FIG. 13. Growth kinetics of *Pediococcus acidilactici* CECT8633 in the absence (control) or presence of different concentrations of Listerine Zero® (C, control without antiseptic; 1:1, not diluted; 1:2, 2-fold dilution; 1:4, 4-fold dilution; 1:8, 8-fold dilution). X-axis=time (t) in hours (h).

As shown in FIGS. 5 and 6, chlorhexidine and chlorhexidine gluconate were the mouthwash antiseptics showing the highest antimicrobial effect as all the strains were inhibited at the highest concentration tested (0.12%, v/v). Similarly to other mouthwash ingredients, *P. gingivalis* and *Streptococcus* sp. were the strains showing the highest susceptibility to chlorhexidine as they were inhibited at any of the concentration tested. *L. brevis* was inhibited by concentrations of 0.12% and 0.06%, but not 0.03%, showing therefore a higher tolerance than *P. gingivalis* and *Streptococcus* sp. *Pediococcus* sp. strains were shown to be the LAB showing the greatest resistance to chlorhexidine. Inhibition halos observed around discs impregnated with chlorhexidine were of 4, 3 and 2 mm for *Pediococcus pentosaceous* CECT8330, *P. acidilactici* CECT8633 and *P. acidilactici* AB134, respectively, wherein the inhibition halo of *P. gingivalis* was 9 mm. Therefore, *Pediococcus acidilactici* strains were particularly resistant to chlorhexidine. Likewise, *Pediococcus* strains were shown to be the strains showing the highest resistance to chlorhexidine gluconate. FIG. 7. clearly illustrate the lower inhibition halo observed for *P. acidilactici* CECT8633 compared with *S. salivarius* K12 and *P. gingivalis* in the presence of chlorhexidine gluconate 0.12%.

In conclusion, it was shown that inhibitory effect of antiseptics was higher for the pathogen *P. gingivalis* as well as for probiotics from *Streptococcus* sp. genus, followed by *Lactobacillus* sp. Probiotics from *Pediococcus* sp. genus were especially resistant to antiseptics, and particularly those probiotics belonging to *Pediococcus acidilactici* species.

Example 3: Tolerance of Lactic Acid Strains to Antiseptics (Liquid Medium Assay)

In order to ascertain whether the growth kinetics of LAC can be affected by the presence of mouthwashes, the inhibitory effect of Listerine Zero® was studied in liquid media. Overnight cultures of probiotic bacteria were prepared as described in EXAMPLE 2. Isolated colonies were used for preparing a bacterial suspension in sterile 0.1 M PBS to reach an optical density corresponding to a Mc. Farland standard of 0.5 (approx. 1.5E+08 CFU/mL). Subsequently, 100-fold dilutions were prepared to obtain a concentration of approximately 1.5E+06 CFU/mL. Listerine Zero® was filtered through 0.22 micrometers and 4 consecutive 2-fold dilutions prepared.

Liquid growth media (140 microliters) suitable for the appropriate growth of each microorganism according to TABLE 1 (EXAMPLE 2) were pipetted in 96-well microplates. Then, 40 microliters of the mouthwash dilution were added followed by 20 microliters of the bacterial suspension containing 1E+06 CFU/mL. Blanks without probiotic and positive controls without ingredients (but PBS) were also prepared. Bacterial growth was assessed by determining the optical density (O.D.) at 550 nm of wells containing probiotic at 24 and 48 h and subtracting the O.D. of wells having the same concentration of mouthwash but without probiotic. The survival ratio was calculated at 48 h by the formula:

$$\text{Survival ratio } (\%) = \frac{(ODp - ODb) - (ODm - ODmb)}{ODp - ODb} * 100$$

wherein $OD_p$ is the optical density of the well inoculated with probiotic but not containing mouthwash (positive control), $OD_b$ is the optical density of the well without probiotic and without mouthwash, $OD_m$ is the optical density of the well with probiotic and with mouthwash, and $OD_{mb}$ is the optical density of the well without probiotic and with mouthwash.

Conditions were Studied in Triplicate.

FIGS. 8-13, depict the growth kinetics of probiotic strains at different concentrations of Listerine Zero®. Results confirm that Listerine reduced the growth of *Streptococcus* strains at all the concentration tested. *S. salivarius* K12 was only able to grow at dilution 1:4 and 1:8, but its growth was drastically reduced compared with the positive control (probiotic without mouthwash). *S. oralis* was able to growth only when the mouthwash dilution of Listerine reached 8 times the original concentration. However, even at this concentration no growth was observed at 24 h and the amount of probiotic was approximately 2-times lower than the positive control at 48 h. The growth ratio of *L. brevis* was in lower than *Streptococcus* strains as no growth was observed until 48 h after inoculation of the medium. However, the tolerance of *L. brevis* CD2 to the mouthwash was confirmed to be higher than *Streptococcus* strains as it was only fully inhibited when the mouthwash was not diluted. The concentration of *L. brevis* CD2 when 2-, 4- and 8-fold dilutions were present in the medium was reduced approximately by 50%.

*Pediococcus* strains were the probiotics showing the highest tolerance to the mouthwash. The presence of Listerine® not diluted fully inhibited the growth of *P. pentosaceus* CECT8330, *P. acidilactici* AB134 and *P. acidilactici* CECT8633 at 24 h. However, *P. acidilactici* AB134 and *P. acidilactici* CECT8633 where the only ones able to growth in the presence of this mouthwash after 48 h.

Figure 14:
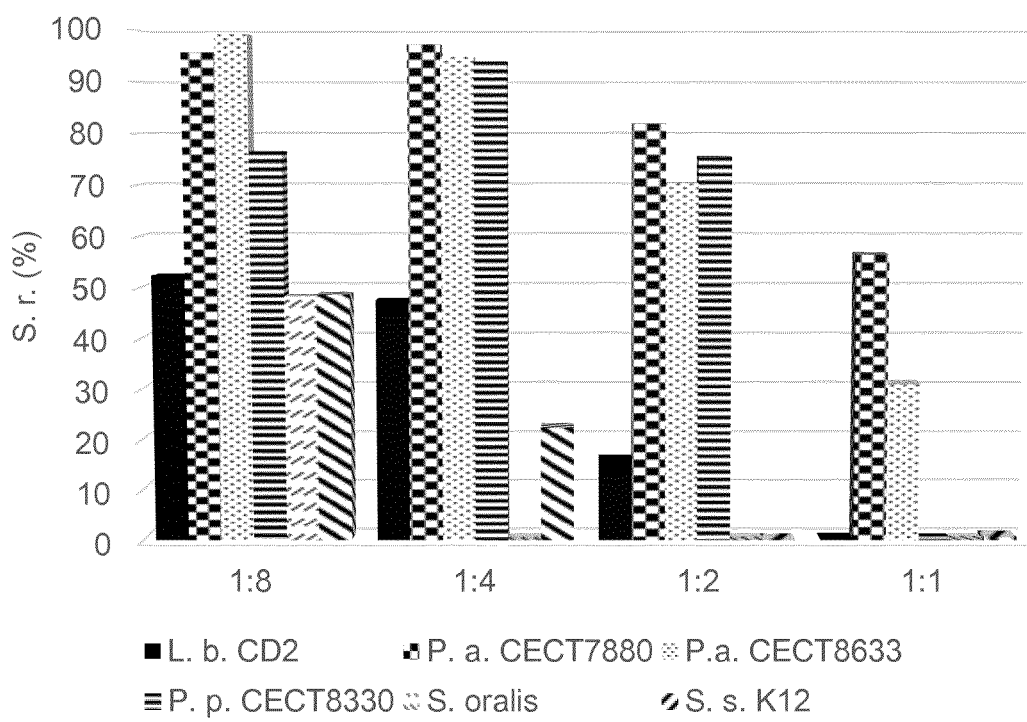
FIG. 14. Survival ratio (S.r) of lactic acid bacteria strains expressed as percentage (mm) when determined by liquid medium assay. *Lactobacillus brevis* CD2 (L.b.CD2); *Pediococcus acidilactici* AB134 (P.a. AB134); *Pediococcus acidilactici* CECT 8630 (P.a. CECT 8630); *Pediococcus pentosaceus* CECT 8330 (P.p. CECT 8330) *Streptococcus oralis; Streptococcus salivarius* K12 (S.s. K12).

FIG. 14 summarizes the survival ratio of the different strains after 48 h. It can be clearly seen how only *Pediococcus acidilactici* strains CECT7780 and CECT8633 were able to grow in the presence of mouthwash not diluted, and how *L. brevis* CD2 and particularly *P. pentosaceus* CECT8330 were also able to when the mouth wash was diluted 2 times. The survival ratio of *Streptococcus* strains was always lower than that of the other probiotic strains at all the concentrations.

Example 4: Antagonistic Activity Against Periodontal Pathogens

The antagonistic capacity of *P. acidilactici* CECT8633 was tested against pathogen species widely associated with gingivitis, periodontitis and halitosis, namely *Fusobacte-*

*rium nucleatum, Treponema denticola* and *Prevotella denticola*. Pathogens were obtained from the Collection of Institute Pasteur (deposit code CIP104988, CIP103919 and CIP104478T, respectively).

*P. acidilactici* CECT8633 was grown on MRS plates at 37° C. and 5% $CO_2$ to confluence. Six-millimeter diameter cylinder sections of the confluents were placed on M20 plates inoculated with *F. nucleatum* and *P. denticola* or M71 plates inoculated with *T. denticola*. The medium of M20 plates was 30 g tryptone, 20 g yeast extract, 0.5 g cysteine hydrochloride, 5 g glucose and 25 mL hemin solution (0.1 g hemin chloride, 4 mL triethanolamine and 96 mL distilled water) per litre). The medium of M71 plates was 15 g tryptone, 5 g yeast extract, 8 g di sodium hydrogen phosphate, 1 g ammonium carbonate, 0.5 g cysteine hydrochloride, 0.03 mL thioglycolic acid, 0.05 mL Tween 80 and 250 mL horse serum per litre. Plates were incubated overnight at 37° C. in anaerobic conditions. Growth inhibitory activity (GI) was calculated subtracting the cylinder diameter (CD, mm) from the inhibition zone diameter (IZD, mm) as follows: GI=(IZD-CD)/2. Results were compared with *S. salivarius* K12 (BLIS Technologies Ltd., New Zealand) and *L. reuteri* ATCC 55730 (GumPeriobalance® (BioGaia, Sweden), which were grown in the same conditions as *P. acidilactici* CECT8633.

Figure 15:
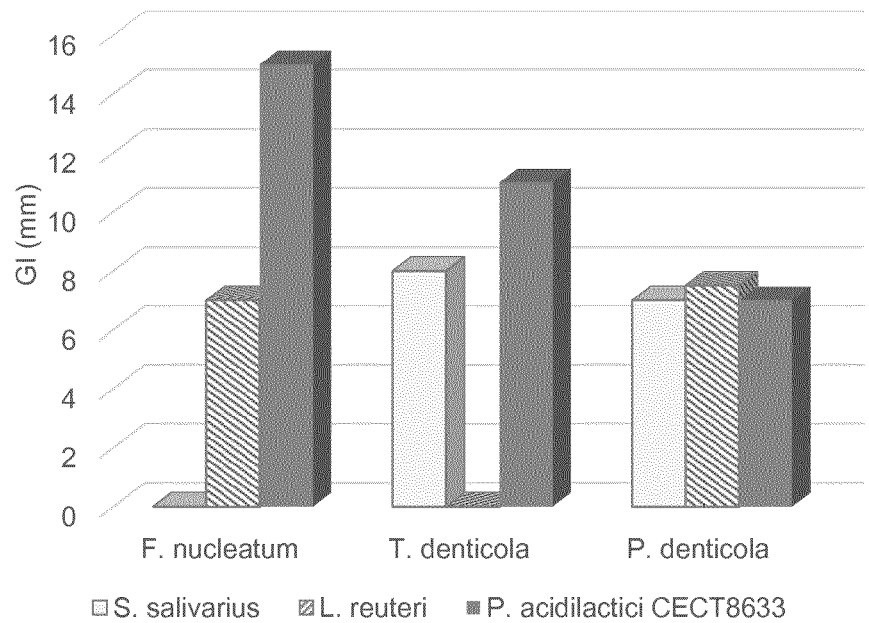
FIG. 15. Antagonistic activity of *Streptococcus salivarius* K12, *Lactobacillus reuteri* ATCC 55730 and *Pediococcus acidilactici* CECT8633 expressed as of growth inhibition (GI) in millimetres against the oral pathogens *Fusobacterium nucleatum, Treponema denticola* and *Prevotella denticola*.

Results are depicted in FIG. 15. *P. acidilactici* CECT8633 showed the capacity to inhibit the growth of the three pathogens tested, which was not the case of *S. salivarius* and *L. reuteri*, which inhibited two of the three pathogens tested. Moreover, *P. acidilactici* CECT8633 showed higher capacity to inhibit the growth of *F. nucleatum* and *T. denticola* than commercial controls.

Example 5: Clinical Efficacy

A double-blind randomized placebo-controlled clinical trial was conducted to assess the safety of LAB strains and their efficacy as probiotics improving parameters associated with gingivitis.

Subjects enrolled in the clinical trial meet all the inclusion and exclusion criteria. Inclusion criteria: 18-55 years of age; male or female (balanced groups); non-smokers (never smokers or former smokers for at least 6 months); subjects with natural occurring gingivitis defined as a mean gingival index (GI)>1.3; no interproximal attachment loss >2 mm at the majority of the sites. Exclusion criteria: Carious lesions and/or inadequate restorations in maxillary lateral incisors, first or second premolars and first molars or adjacent teeth, interfering with dental plaque removal in the sites of interest; subjects currently undergoing dental treatment; subjects currently undergoing orthodontic therapy or wearing occlusal bite-guards; subjects suffering any systemic disease or condition which may affect the response of gingival tissues or the ability to perform adequate plaque control (pregnancy, diabetes, quantitative and/or qualitative polymorphonuclear cell defects, other immune system disorders, etc.); subjects having medications that could interfere with the gingival response; subjects on antibiotics or antiseptics within the 2 months previous to the study; subjects using probiotic products for oral health within the 2 months previous to the study; history of hypersensitivity or allergy to any component of the treatment products.

At day 0, a professional oral hygiene (scale and polish) was conducted to all the subjects. Fluoride tooth paste was provided as well as indications to brush the teeth twice per day to standardize the oral hygiene habits.

Subjects were randomized assigned into one of the following two treatments:

TABLE 3

Study treatments

| | PROBIOTIC | PLACEBO |
|---|---|---|
| Composition (per tablet): | Probiotic mixture *Lactobacillus plantarum* CECT7481, *Lactobacillus brevis* CECT7480 and *Pediococcus acidilactici* CECT8633): 125 mg Guar gum (E-412): 80.00 mg Sorbitol: 691.20 mg Hydrogenated cotton oil: 18.32 mg Mint flavour: 20.00 mg | Trehalose: 125 mg Guar gum (E-412): 80.00 mg Sorbitol: 691.20 mg Hydrogenated cotton oil: 18.32 mg Mint flavour: 20.00 mg |
| Dose: | 2 tablets/day | 2 tablets/day |
| Administration route: | Oral | Oral |
| Galenic form: | Oral dispersable tablets | Oral dispersable tablets |

Neither the patients nor the facultative knew to which treatment each subject was assigned. Dispersible tablets had the same aspect and the cases containing them included the code of the study and the corresponding identification number of the subject. The investigator provided the participants with the cases containing the tablets, which had the same aspect. The treatment assigned to each volunteer (A o B) was registered in a dated register. The randomization was only revealed at the end of the study, once data has been analysed, or if there were any relevant event which forces to break the blinding. Subjects consumed the corresponding product for 6 weeks. The oral dispersible tablets were allowed to slowly melt in the mouth, once finished each tooth-brushing (twice a day). After consuming the product, participants were not allowed to clean their teeth or to have any food or drink (other than water) during 1 hour after tablet consumption. Subjects were asked to report intake of tablets by filling daily a questionnaire for adherence to protocol. This was returned to examiners together with boxes with unused tablets, in order to study the compliance of each patient.

The primary endpoint was Gingival index (GI), according to a modification of the method of Loe & Silness (1963) without the bleeding on probing component [Löe, H. et al. "Periodontal disease in pregnancy". *Acta Odontologica Scandinavica* 1963, vol. 21, pp. 533-551]. The mean GI was calculated by dividing the sum of all scores of each tooth by the total number of examined teeth.

At day 0 (baseline) gingival index (GI) was determined before the professional oral hygiene (scale and polish). The same variable was determined after 6 weeks.

At day 0 (baseline) and week 6 (end of the study) just before the clinical examination, supragingival plaque samples were collected, one for each quadrant (maxillary left-right/mandibular left-right) and pooled. Supragingival plaque was obtained using sterile paper points left in place for 10 seconds. The sampled paper points was pooled and transferred to a microcentrifuge tube containing 200 µl of TE buffer (10 mm tris[hydroxymethyl]-methylamine chloride, 1 mm ethylenediamine tetraacetic acid) and stored at −20° C. until analyzed. Real time PCR based on Taqman Probes with specific primers for six putative periodontal pathogens (*Aggregatibacter actinomycetemcomitans; Porphyromonas gingivalis; Tannerella forsythia; Fusobacterium* species; *Streptococcus oralis; Campylobacter rectus*) was performed.

Primary and secondary variables were analysed with SAS. All the analysis was conducted under intention-to-treat (ITT) and per-protocol (PP) criteria. The data were checked for normality Shapiro-Wilks test. If data were parametrically distributed, differences in primary and secondary variables between groups will be determined by analysis of variance (ANOVA). In order to know, the exact nature of differences between groups, post hoc test were determined (e.g. Duncan's multirange test). If data were not parametrically distributed, the comparison of quantitative variables were carried out by non-parametric tests (Wilcoxon for paired data and Mann-Whitney for independent data). In all hypothesis tests, the null hypothesis assumed equality between treatment groups and rejected when the P values was lower than 0.05. This means that significant differences were considered when a or type I error was <0.05.

Fifty-nine patients were assessed for eligibility and randomized into probiotic group (n=30) or placebo group (n=29). Baseline characteristics of the patients were as summarized in TABLE 4:

TABLE 4

Demographic characteristics of study population

| | Probiotic N = 30 | Control N = 29 | Total N = 59 |
|---|---|---|---|
| Age (years) p-value = 0.7805 (Wilcoxon Rank-sum Test) | | | |
| N | 29 | 29 | 58 |
| N missing | 1* | 0 | 1 |
| Mean (STD) | 30.91 (12.20) | 32.50 (13.62) | 31.71 (12.84) |
| CI95% (Mean) | (26.27, 35.55) | (27.33, 37.68) | (28.33, 35.08) |
| Range (Min, Max) | (17.76, 55.33) | (17.70, 65.70) | (17.70, 65.70) |
| Median | 26.26 | 28.20 | 27.49 |
| IQR (Q1, Q3) | (21.47, 38.36) | (21.34, 37.45) | (21.45, 38.36) |
| Gender p-value = 0.7106 (Test ChiSq) | | | |
| Female | 19 (63.3%) | 17 (58.6%) | 36 (61.0%) |
| Male | 11 (36.7%) | 12 (41.4%) | 23 (39.0%) |

*Missing data but in ranges of selection criteria

The 94.2% of patients took at least 75% of treatment, 89.7% in probiotic group and 100.0% in control group. There were no differences in treatment compliance between groups.

At week 6, the number of individual tooth surfaces with a GI score of 3 ("number of individual GI scores=3") was lower in probiotic group than control group (n=0 (0.0%) vs. n=5 (0.2%), p-value=0.0418).

Figure 16:
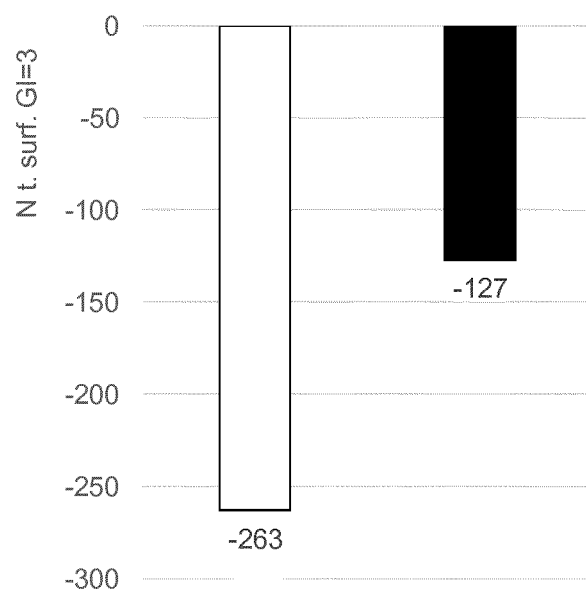
FIG. 16. Reduction in the number of teeth surfaces showing the worst gingival index score (GI=3) compared with the beginning of the study. Black bar denotes the group of subjects following a standard oral care procedure (placebo group); White bar denotes the group of subjects following a standard oral care procedure plus probiotic (probiotic group). Y-axis=number of teeth surfaces with a gingival index equal to 3 (N t. surf. GI=3).
Figure 17:
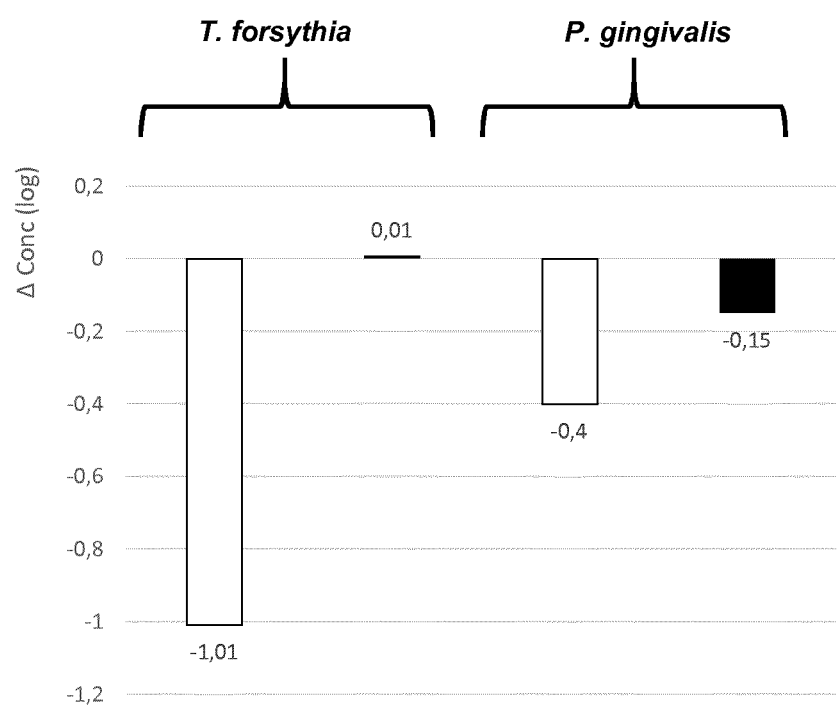
FIG. 17. Change in the concentration of pathogens *Tannerella forsythia* and *Porphyromonas gingivalis* (Δ Conc=concentration at the end of the study—concentration at the beginning of the study expressed as logarithm). Black bars denote the group of subjects following a standard oral care procedure (placebo group); White bars denote the group of subjects following a standard oral care procedure plus probiotic (probiotic group).

The amount of change between baseline and endpoint (baseline-week 6) was also significantly higher for the Probiotic than for the Control group (standard care) (P<0.01, regardless of ITT or PP analysis) (FIG. 16) Treatment with probiotic-containing tablets was correlated with a significant reduction in the levels of *Tannerella forsythia* as well as *Porphyromonas gingivalis* (FIG. 17).

In conclusion probiotic tablets were able to reduce the number of sites presenting severe inflammation in comparison with professional oral hygiene alone, in gingivitis patients. The use of the probiotic presented also a significant microbiological impact as it was associated with a reduction in counts of *T. forsythia* and *P. gingivalis*, pathogens widely recognized as negatively involved in the course of gingivitis, and which displayed the strongest correlation to the number of sites presenting severe inflammation among the pathogenic bacteria measured in the study population.

Example 6: Formulation in Oral Dispersible Tablets

Oral Dispersible Tablets have the Following Composition:
125 mg *Pediococcus acidilactici* CECT8633
1.3 µg colecalciferol (Vitament D3)
20 mg mint flavour
80 mg guar gum
689.53 mg sorbitol
9.35 syloid
9.35 magnesium stearated The formulation is suitable for slowly melting in the oral cavity. Probiotic concentration at the end of the shelf-life is 1E+09 CFU per tablet.

Alternatively, the tablet comprises *Lactobacillus plantarum* CECT7481, *Lactobacillus brevis* CECT7480 in addition to *Pediococcus acidilactici* CECT8633.

Example 7: Formulation in Oral Gel

Vials Contain 500 mg of Powder Containing the Following Ingredients:
*Pediococcus acidilactici* CECT8633 (Minimum concentration of probiotic at the end of the shelf-life is 6E+09 CFU/vial)
Clorofilin E141ii (4%, w/w)
Guar gum (5.2% w/w).

Example 8: Formulation in Chewing Gums

Chewing Gums Contain the Following Composition:
1340.68 of gum base (Health in gum PWD-03)
125 mg *Lactobacillus plantarum* CECT7481, *Lactobacillus brevis* CECT7480 and *Pediococcus acidilactici* CECT8633 (ratio 1:1:1)
31.52 mg encapsulated flavour
47.28 mg powder flavor
12.61 mg liquid flavor
24.0 mg magnesium stearate
15.75 mg silicon dioxide
1.89 mg aspartame
1.26 mg acesulfam K Example 9: Formulation in Toothpaste Toothpaste Formulation is Composed by:
125 mg of *Pediococcus acidilactici* CECT8633
0.12 clorhexidine digluconate
1 g xylitol
0.5 g α-tocopherol acetate
100 g of excipient
Alternatively, Toothpaste Formulation is:
*Pediococcus acidilactici* CECT8633 to achieve a final concentration of 1E+09
CFU at the end of the shelf-life.
0.04 g glycerhetinic acid
0.16 g sodium fluoride
8 g PEG-12
0.8 g zeolite
5.6 g silica
1.6 g polyglyceryl-5 laurate
0.8 g xylitol
0.48 g menthol
0.4 g sodium saccharin
0.4 g sodium benzoate
0.24 g *eucalyptus globulus*
0.08 g cyclodextrin 0.96 g hydroxypropulcellulose
30.56 g butylene glycol Example 10: Formulation in Mouthwash Mouthwash combines the ingredients present in a delivery cap and a vial. The delivery caps contained 100 mg of freeze-dried probiotic strain CECT8633 (1-2E+09 cfu per delivery cap), magnesium stearate (2.2 mg) (in this description referred as e.g. anticaking agent and anti-adherent) and silicon dioxide (0.5 mg) (referred in this description as anticaking agent). The vial contains 10 mL mouthwash composed by contained 0.092% eucalyptol, 0.042% menthol, 0.06% methylsalicylate, 0.064% thymol, and 27% ethanol (w/v).

By pushing the cap, the probiotic is released in the liquid contained in the vial. The composition is mixed and then used for gargling for 1 minute.

Example 11. Fermentation and Post-Treatment of Lactic Acid Bacteria

Post-treat biomass used as raw material was obtained by a manufacturing process that included the steps of fermenting and freeze-drying. A mother culture was prepared by inoculating 80 mL of MRS broth medium with the *P. acidilactici* strains. The inoculated medium was fermented at 37° C. in microaerophilic conditions for 48 h. The resulting culture was used for inoculating 600 litres of MRS broth medium in a ratio of about 1-2% of inoculum per total volume of broth medium. The resulting medium was cooled at 3-5° C. and centrifuged in order to eliminate most of the water present in the broth. Cryoprotectants were added to the concentrated culture and the resulting mixture freeze-dried at −45° C.

BIBLIOGRAPHIC REFERENCES

Castalonga M, et al. "The oral microbiome and the immunobiology of periodontal disease and caries" *Immunology Letters* 214, vol. 12, pp. 22-38.

Dann A B, et al. "Triclosan: environmental exposure, toxicity and mechanisms of action" Journal of Applied Toxicology 2011, vol. 31, pp. 285-311.

Flötra, L. et al. "Side effects of chlorhexidine mouth washes". Scand J Dent Res 1971, vol. 73, p. 119-125.

Gruner, D. et al. "Probiotics for managing caries and periodontitis: Systematic Review and Meta-Analysis". *J Dent* 2016, vol. 48, pp. 16-15.

Haffajee, A D. et al. "Microbial etiological agents of destructive periodontal Diseases" *Periodontology* 2000. 1994, vol. 5, pp. 78-11.

Hallstroem, H. et al. "Effect of probiotic lozenges on inflammatory reactions and oral biofilm during experimental gingivitis". *Acta Odontologica Scandinavica* 2013, vol. 71, p. 828-833.

Jin L J et al. "Global burden of oral diseases: emerging concepts, management and interplay with systemic health" *Oral Diseases* 2016

Laudenbach et al. "Common Dental and Periodontal Diseases. Evaluation and management" *Med Clin N Am* 2014, vol. 98, pp. 1239-1260

Maekawa, T. et al. "Topical treatment with probiotic *Lactobacillus brevis* CD2" inhibits experimental periodontal inflammation and bone loss" J Periodont Res 214, vol. 44, p. 785-791

Nadkerny P V, et al. "A comparative evaluation of the efficacy of probiotic and chlorhexidine mouthrinses on clinical inflammatory parameters of gingivitis: A randomized controlled clinical study" *J Indian Soc Periodontol* 2015 vol 16, pp. 633-639

Penala, S. et al. "Efficacy of local use of probiotics as an adjunct to scaling and root planing in chronic periodontitis and halitosis: A randomized controlled trial" *J Res Pharm Pract.* 2016 Vol. 5(2), pp. 86-93.

Szkaradkiewicz, A. K. et al. "Effect of Oral Administration Involving a Probiotic Strain of *Lactobacillus reuteri* on Pro-Inflammatory Cytokine Response in Patients with Chronic Periodontitis". Arch Immunol Ther Exp (Warsz) 2014, vol. 62, p. 495-500

Teughels, W. et al. "Clinical and microbiological effects of *Lactobacillus reuteri* probiotics in the treatment of chronic periodontitis: a randomized placebo-controlled study" J of clinical periodontology 2013, vol. 40 p. 1025-35.

Toiviainen, A. et al., "Impact of orally administered lozenges with *Lactobacillus rhamnosus* GG and *Bifidobacterium animalis* subsp. *lactis* BB-12 on the number of salivary *mutans* streptococci, amount of plaque, gingival inflammation and the oral microbiome in healthy adults". *Clin Oral Investig* 2015, vol. 19, p. 77-83.

Vlachojannis C, et al. "A Preliminary Investigation on the Antimicrobial Activity of Listerine®, Its Components, and of Mixtures Thereof" *Phytotherapy research* 2015, vol. 29, pp. 1590-1594

Vlachojannis C, et al. "Listerine® Products: An update on the efficacy and safety" *Phytotheraphy Research* 2016, vol. 30, pp. 367-373

Yanine, N. et al. "Effects of probiotics in periodontal diseases: a systematic review". Clinical oral investigations 2013, vol. 17, p. 1627-34

L. Dunn et al (Journal of Food Science • Vol. 81, Nr. 2, 2016, pages M438-M444)

WO2017012905A1 (AB-BIOTICS)

The invention claimed is:

1. A method of treatment of a disorder in the oral cavity in a subject comprising administering to the subject a *Pediococcus* strain in combination with at least one antiseptic, wherein the *Pediococcus* strain has the ability to tolerate at least one antiseptic selected from the group consisting of:
   a) triclosan;
   b) an essential oil comprising at least an individual constituent selected from the group consisting of menthol, eucalyptol, thymol and methyl salicylate; and
   c) an individual constituent selected from the group consisting of menthol, eucalyptol, thymol and methyl salicylate,
   wherein the *Pediococcus* strain is considered to have the ability to tolerate the antiseptic when a inhibition halo determined by disc diffusion assay observed for the *Pediococcus* strain is smaller than a inhibition halo of *Porphyromonas gingivalis*, wherein the antiseptic is in a concentration to observe an inhibition of *Porphyromonas gingivalis*, wherein the *Pediococcus* strain and the antiseptic are formulated for a separate, sequential, concomitant administration or in admixture, wherein the *Porphyromonas gingivalis* is *Porphyromonas gingivalis* DSM20709, and wherein the *Pediococcus* strain is a *Pediococcus acidilactici* strain.

2. The method according to claim 1, wherein the *Pediococcus acidilactici* strain is a strain of *Pediococcus acidilactici* deposited in the Spanish Type Culture Collection under the accession number CECT 8633.

3. The method according to claim 1, wherein the *Pediococcus* strain is in combination with at least one antiseptic selected from the group consisting of triclosan; an essential oil comprising at least an individual constituent selected from the group consisting of menthol, eucalyptol, thymol and methyl salicylate; an individual constituent selected from the group consisting of menthol, eucalyptol, thymol and methyl salicylate; and bisguadines.

4. The method according to claim 3, wherein the *Pediococcus* strain is in combination with at least one antiseptic selected from the group consisting of triclosan; and an essential oil comprising at least an individual constituent selected from the group consisting of menthol, eucalyptol, thymol and methyl salicylate.

5. The method according to claim 3, wherein the antiseptic is formulated in the form of a personal care product, together with acceptable excipients and/or carriers, and the *Pediococcus* strain is formulated in the form of a personal care product or a pharmaceutical product, together with acceptable excipients and/or carriers.

6. The method according to claim 5, wherein the personal care product is an oral care product.

7. The method according to claim 6, wherein the oral care product is a toothpaste, oral gel, oral spray, mouth rinse or oral dispersible tablet.

8. The method according to claim 1, wherein the antiseptic and *Pediococcus* strain are administered separately for a time interval and wherein the time interval is no longer than 1 hour.

9. The method according to claim 8, wherein the subject to be treated is instructed to gargle their mouth with a mouthwash containing an antiseptic for 30-60 seconds and then the mouthwash is split out and oral tablet containing the *Pediococcus* strain is then introduced in the mouth and allowed to melt slowly.

10. The method according to claim 1, wherein the disorder in the oral cavity is caused by oral pathogens.

11. A composition comprising a strain belonging to *Pediococcus acidilactici* species deposited in the Spanish Type Culture Collection under accession number CECT 8633, wherein the composition is formulated in the form of a personal care product or a pharmaceutical product, together with acceptable excipients and/or carriers.

12. A method to obtain a mutant of *Pediococcus acidilactici* deposited in the Spanish Type Culture Collection under accession number CECT 8633, wherein the method comprises using the deposited CECT 8633 strain as starting material and applying mutagenesis, and wherein the obtained mutant retains or enhances at least the ability of the deposited strain to tolerate antiseptics.

13. A composition comprising: a *Pediococcus* strain in combination with at least one antiseptic, wherein the *Pediococcus* strain has the ability to tolerate at least one antiseptic selected from the group consisting of:
a) triclosan;
b) an essential oil comprising at least an individual constituent selected from the group consisting of menthol, eucalyptol, thymol and methyl salicylate; and
c) an individual constituent selected from the group consisting of menthol, eucalyptol, thymol and methyl salicylate,
wherein the *Pediococcus* strain is considered to have the ability to tolerate the antiseptic when a inhibition halo determined by disc diffusion assay observed for the *Pediococcus* strain is smaller than a inhibition halo of *Porphyromonas gingivalis*, wherein the antiseptic is in a concentration to observe an inhibition of *Porphyromonas gingivalis*, wherein the *Pediococcus* strain and the antiseptic are formulated for a separate, sequential, concomitant administration or in admixture, wherein the *Porphyromonas gingivalis* is *Porphyromonas gingivalis* DSM20709, and wherein the *Pediococcus* strain is a *Pediococcus acidilactici* strain deposited in the Spanish Type Culture Collection under accession number CECT 8633.

* * * * *

SEQUENCE LISTING

```
<160> NUMBER OF SEQ ID NOS: 1

<210> SEQ ID NO 1
<211> LENGTH: 1422
<212> TYPE: DNA
<213> ORGANISM: Pediococcus acidilactici

<400> SEQUENCE: 1
gcagtcgacg acttccgtta attgattatg acgtgcttgc actgaatgag attttaacac      60
gaagtgagtg gcggacgggt gagtaacacg tgggtaacct gcccagaagc agggggataac     120
```

-continued

```
acctggaaac agatgctaat accgtataac agagaaaacc gcctggtttt cttttaaaag    180
atggctctgc tatcacttct ggatggaccc gcggcgcatt agctagttgg tgaggtaacg    240
gctcaccaag gcgatgatgc gtagccgacc tgagagggta atcggccaca ttgggactga    300
gacacggccc agactcctac gggaggcagc agtagggaat cttccacaat ggacgcaagt    360
ctgatggagc aacgccgcgt gagtgaagaa gggtttcggc tcgtaaagct ctgttgttaa    420
agaagaacgt gggtgagagt aactgttcac ccagtgacgg tatttaacca gaaagccacg    480
gctaactacg tgccagcagc cgcggtaata cgtaggtggc aagcgttatc cggatttatt    540
gggcgtaaag cgagcgcagg cggtctttta agtctaatgt gaaagccttc ggctcaaccg    600
aagaagtgca ttggaaactg ggagacttga gtgcagaaga ggacagtgga actccatgtg    660
tagcggtgaa atgcgtagat atatggaaga acaccagtgg cgaaggcggc tgtctggtct    720
gtaactgacg ctgaggctcg aaagcatggg tagcgaacag gattagatac cctggtagtc    780
catgccgtaa acgatgatta ctaagtgttg gagggtttcc gcccttcagt gctgcagcta    840
acgcattaag taatccgcct ggggagtacg accgcaaggt tgaaactcaa aagaattgac    900
ggggcccgc acaagcggtg gagcatgtgg tttaattcga agctacgcga agaaccttac    960
caggtcttga catcttctgc caacctaaga gattaggcgt tcccttcggg acagaatgac   1020
aggtggtgca tggttgtcgt cagctcgtgt cgtgagatgt tgggttaagt cccgcaacga   1080
gcgcaaccct tattactagt tgccagcatt cagttgggca ctctagtgag actgccggtg   1140
acaaaccgga ggaaggtggg gacgacgtca aatcatcatg ccccttatga cctgggctac   1200
acacgtgcta caatggatgg tacaacgagt cgcgaaaccg cgaggtttag ctaatctctt   1260
aaaaccattc tcagttcgga ctgtaggctg caactcgcct acacgaagtc ggaatcgcta   1320
gtaatcgcgg atcagcatgc cgcggtgaat acgttcccgg gccttgtaca caccgcccgt   1380
cacaccatga gagtttgtaa cacccaaagc cggtggggta ac                       1422
```